(12) United States Patent
Bhattacharyya et al.

(10) Patent No.: US 7,935,834 B2
(45) Date of Patent: May 3, 2011

(54) CATALYSTS FOR MALEIC ACID HYDROGENATION TO 1,4-BUTANEDIOL

(75) Inventors: Alakananda Bhattacharyya, DuPage, IL (US); Maynard D. Manila, DuPage, IL (US)

(73) Assignee: ISP Investments Inc., Wilmington, DE (US)

( * ) Notice: Subject to any disclaimer, the term of this patent is extended or adjusted under 35 U.S.C. 154(b) by 742 days.

(21) Appl. No.: 10/883,106

(22) Filed: Jul. 1, 2004

(65) Prior Publication Data

US 2006/0004212 A1    Jan. 5, 2006

(51) Int. Cl.
*C07D 307/60* (2006.01)
*C07D 307/08* (2006.01)
*C07C 29/147* (2006.01)

(52) U.S. Cl. ......... 549/325; 549/326; 549/508; 568/864

(58) Field of Classification Search .................. 549/325, 549/326, 508; 568/864
See application file for complete search history.

(56) References Cited

U.S. PATENT DOCUMENTS

| | | | |
|---|---|---|---|
| 4,096,156 A | 6/1978 | Freudenberger et al. | 260/343.6 |
| 4,446,073 A | 5/1984 | Qualeatti et al. | 260/409 |
| 4,524,225 A | 6/1985 | Qualeatti et al. | 568/885 |
| 4,550,185 A | 10/1985 | Mabry et al. | 549/508 |
| 4,609,636 A | 9/1986 | Mabry et al. | 502/183 |
| 4,782,167 A | 11/1988 | Rao et al. | 549/326 |
| 4,985,572 A | 1/1991 | Kitson et al. | 549/326 |
| 5,354,898 A | 10/1994 | Schroeder | 562/485 |
| 5,362,908 A | 11/1994 | Schroeder et al. | 562/487 |
| 5,473,086 A | 12/1995 | Budge et al. | 549/509 |
| 5,616,792 A | 4/1997 | Bartos et al. | 562/486 |
| 5,698,749 A | 12/1997 | Pedersen et al. | 568/864 |
| 5,756,833 A | 5/1998 | Rosen et al. | 562/486 |
| 5,969,164 A | 10/1999 | Budge et al. | 549/508 |
| 5,985,789 A | 11/1999 | Tooley et al. | 502/326 |
| 6,486,367 B1 | 11/2002 | Budge et al. | 568/864 |

FOREIGN PATENT DOCUMENTS

| | | |
|---|---|---|
| CA | 1070711 | 1/1980 |
| DE | 1534232 | 2/1977 |
| DE | 10252282 | 5/2004 |
| EP | 0276012 | 7/1988 |
| EP | 0400904 | 12/1990 |
| GB | 1551741 | 8/1979 |
| JP | 782189 | 3/1995 |

OTHER PUBLICATIONS

Besson et al, Applied Cataysis A: General, vol. 250, p. 117-124 (1983).*
M. Bankmann, R. Brand, B. H. Engler and J. Ohmer, "Forming of High Surface Area TiO2 to Catalyst Supports," Catalysis Today, vol. 14, pp. 225-242 (1992).
M. Che, O. Clause and Ch. Marcilly, "Impregnation and Ion Exchange," Handbook of Heterogeneous Catalysis, vol. 1, pp. 191-207, Edited by: G. Ertl, H. Knozinger, J. Weitkam, ISPN: 352729212-8 (1997 Edition).
International Search Report, PCT/US2005/023306 (mailed Dec. 23, 2005; published Jan. 19, 2006).
International Preliminary Report on Patentability, PCT/US2005/023306 (Jan. 9, 2007).
Bibliographic information, German 10252282, from Thomson Innovation Record View (May 27, 2004).
Communication (Examination Report), European Application No. 05763765.4 (Oct. 29, 2007).
Zhang, J. et al., "Surface Phase Transformation and Photocatalysis of $TiO_2$ Studied by UV Raman Spectroscopy," North American Catalysis Society, 20th North American Meeting, Houston, Texas (Jun. 17-22, 2007).
Santos, J.G. et al., "Synthesis of nanocrystalline rutile-phase titania at low temperatures," *Materials Science-Poland*, vol. 27, No. 4/1, pp. 1067-1076 (2009).

* cited by examiner

*Primary Examiner* — Bernard Dentz
(74) *Attorney, Agent, or Firm* — William J. Davis; Thompson Hine LLP

(57) ABSTRACT

This invention relates to a process for catalytically hydrogenating a hydrogenatable precursor in contact with a hydrogen-containing gas and a hydrogenation catalyst comprising one or more active hydrogenation catalyst components on a support comprising titanium dioxide in the rutile crystalline phase to produce 1,4-butanediol and, optionally, gamma-butyrolactone and/or tetrahydrofuran.

31 Claims, No Drawings

CATALYSTS FOR MALEIC ACID HYDROGENATION TO 1,4-BUTANEDIOL

BACKGROUND OF THE INVENTION

The present invention relates to a process for catalytically hydrogenating a hydrogenatable precursor in contact with a hydrogen-containing gas and a hydrogenation catalyst comprising one or more active hydrogenation catalyst components on a support comprising titanium dioxide in the rutile form to produce 1,4-butanediol (BDO) and, optionally, gamma-butyrolactone (GBL) and/or tetrahydrofuran (THF).

This invention also relates to a process for the hydrogenation of maleic acid to 1,4-butanediol and, optionally, gamma-butyrolactone and/or tetrahydrofuran wherein selective reduction of maleic acid to succinic acid, is achieved in the first step of the hydrogenation process by using a catalyst supported on titanium dioxide in the rutile form and selective reduction of the succinic acid is achieved in the second step of the hydrogenation process by using a hydrogenation catalyst comprising one or more active hydrogenation catalyst components supported on titanium dioxide in the rutile form, a hydrogenation catalyst supported on carbon, or mixtures thereof.

This invention further relates to a process for the production of succinic acid or succinic anhydride by the hydrogenation of maleic acid to produce succinic acid using a hydrogenation catalyst comprising one or more active hydrogenation catalyst components supported on titanium dioxide in the rutile form, and then, optionally, dehydrating the succinic acid to convert the succinic acid to succinic anhydride.

In one embodiment, at least about one weight percent, preferably at least about 80 weight percent, more preferably at least about 90 weight percent, more preferably at least about 95 weight percent and more preferably 100 weight percent of the titanium dioxide catalyst support is in the rutile crystalline phase.

1,4-Butanediol (BDO) is a commercial commodity with a plurality of uses. For example, 1,4-butanediol is used in the production of polybutylene terepthalate and reaction-injected molded (RIM) urethanes. 1,4-butanediol is also used in polytetramethylene ether glycol (PTMEG), which is employed as a raw material for spandex. Tetrahydrofuran is a useful solvent for natural and synthetic resins and is a valuable intermediate in the manufacture of a number of chemicals and plastics. Gamma-butyrolactone is an intermediate for the synthesis of butyric acid compounds, polyvinylpyrrolidone and methionine. Gamma-butyrolactone is a useful solvent for acrylate and styrene polymers and also a useful ingredient of paint removers and textile assistants. 1,4-butanediol (a.k.a. 1,4-butylene glycol) is useful as a solvent, a humectant, an intermediate for plasticizers and pharmaceuticals, a cross-linking agent for polyurethane elastomers, a precursor in the manufacture of tetrahydrofuran, and is used to make terephthalate plastics.

It is well known that 1,4-butanediol may be obtained by the catalytic hydrogenation of maleic acid, maleic anhydride and similar hydrogenatable compounds. In such processes, aqueous maleic acid is fed with hydrogen to a reactor containing a fixed bed catalyst. The reaction products containing 1,4-butanediol, tetrahydrofuran and gamma-butyrolactone are then recovered and purified by conventional means.

British Patent No. 1,534,232 teaches the hydrogenation of carboxylic acids, lactones or anhydrides using a hydrogenation catalyst consisting of palladium and rhenium on a carbon support. U.S. Pat. Nos. 4,550,185 and 4,609,636 teach a process of making tetrahydrofuran and 1,4-butanediol by hydrogenating maleic acid, maleic anhydride or another hydrogenatable precursor in the presence of a catalyst comprising palladium and rhenium on a carbon support wherein the palladium and rhenium were present in the form of crystallites having an average palladium crystallite size of about 10 to 25 nm and an average rhenium crystallite size of less than 2.5 nm. The preparation of this catalyst is characterized by the deposition and reduction of the palladium species on the carbon support followed by the deposition and reduction of the rhenium species on the palladium impregnated carbon support.

U.S. Pat. No. 4,985,572 teaches a process for the catalytic hydrogenation of a carboxylic acid or an anhydride thereof to the corresponding alcohol and/or carboxylic acid ester using a catalyst comprising rhenium, palladium and silver on a carbon support. The preparation of this catalyst is characterized by the simultaneous deposition of palladium and silver on the carbon support followed by a high temperature (600° C.) heat treatment. Rhenium was then deposited on the palladium/silver impregnated carbon support. The resulting catalyst was then reduced.

U.S. Pat. No. 5,473,086 discloses a process for the production of tetrahydrofuran and 1,4-butanediol comprising catalytically hydrogenating a hydrogenatable precursor in contact with a hydrogen-containing gas and a hydrogenation catalyst comprising palladium, silver and rhenium on a carbon support to produce a product comprising a major portion of 1,4-butanediol wherein the hydrogenation catalyst is prepared by the steps of (i) impregnating the carbon support with a source of palladium, silver and rhenium in one or more impregnation steps comprising contacting the carbon support with a source of palladium, silver and rhenium, said palladium, silver and rhenium being in at least one solution; (ii) drying the impregnated carbon support to remove solvent after each impregnation step; and (iii) heating the impregnated carbon support at a temperature of about 100° C. to about 350° C. under reducing conditions.

U.S. Pat. No. 5,698,749 discloses a process for the production of 1,4-butanediol comprising catalytically hydrogenating a hydrogenatable precursor in contact with a hydrogen-containing gas and a hydrogenation catalyst comprising at least one noble metal of Group VIII of the Periodic Table and at least one of rhenium, tungsten and molybdenum deposited on a carbon support, wherein the carbon support has been contacted with an oxidizing agent selected from the group consisting of nitric acid, hydrogen peroxide, sodium hypochlorite, ammonium persulfate and perchloric acid prior to the deposition of the metals.

U.S. Pat. No. 5,969,164 discloses a catalyst for the hydrogenation of maleic acid, maleic anhydride or other hydrogenatable precursor to 1,4-butanediol and tetrahydrofuran has been discovered. This hydrogenation catalyst comprises palladium, silver, rhenium and at least one of iron, aluminum, cobalt and mixtures thereof, all on a carbon support.

U.S. Pat. No. 6,486,367 discloses a process for the production of 1,4-butanediol comprising catalytically hydrogenating a hydrogenatable precursor in contact with a hydrogen-containing gas and a hydrogenation catalyst comprising at least one noble metal of Group VIII of the Periodic Table, selected from the group consisting of palladium, ruthenium, rhodium, osmium, iridium and platinum wherein iron is added to the hydrogenatable precursor. The catalyst is supported on carbon.

Carbon has generally been used as the support material for the hydrogenation metal in the catalyst employed in prior hydrogenation processes for preparing 1,4-butanediol. A common disadvantage of the use of a carbon support is that carbon fines are often generated during commercial operations. The generation of such fines can be minimized but generally cannot be completely avoided. During the hydrogenation process, such particulates can plug the void spaces in the catalyst through which the reactants must flow and thereby cause interruptions in the process.

Carbon supports may flake under the reaction conditions. Flaking or breaking of the carbon support can cause a higher pressure differential (delta P) because the pores or void spaces in the catalyst are blocked so that the hydrogenatable precursor feed cannot pass through effectively. This can lead to crushing of the catalyst.

For this reason, it is highly desirable to use other materials as the support material in the catalyst employed in the maleic acid hydrogenation process. However, because of the highly corrosive conditions under which the aforesaid hydrogenation is performed, it has proven difficult to develop suitable non-carbon catalyst supports for use in the hydrogenation catalyst. Hot aqueous solutions of maleic acid may dissolve or attack and pit some types of supporting materials.

U.S. Pat. No. 4,782,167 discloses a process for producing butyrolactones, butanediols, and mixtures thereof comprising hydrogenating a hydrogenatable precursor in the presence of an aqueous reaction medium and a catalyst comprising palladium or combinations thereof with rhenium and at least one support selected from the oxides of titanium, zirconium, and hafnium. There is no disclosure of the use of titanium dioxide in the rutile crystalline phase as a catalyst support.

Canadian Patent No. 1070711 discloses a process for the production of 1,4-butanediol from maleic anhydride, maleic acid or mixtures thereof in one step in the presence of catalysts comprising simultaneously elements of subgroup VII or compounds thereof, or elements of subgroup VIII or elements thereof, or mixtures of these elements and compounds. The catalyst elements can be manganese, rhenium, ruthenium, rhodium, palladium, osmium, iridium, and platinum; and rhenium, palladium and platinum are used preferably. The catalyst elements can be palladium and rhenium. The catalyst can be on a support, which can be silicon dioxide, titanium dioxide, silicon dioxide-aluminum oxide, carbon, thorium oxide, zirconium oxide, silicon carbide, spinels, and aluminum oxide. The solvent can be water when maleic acid is the starting material. There is no disclosure of the use of titanium dioxide in the rutile crystalline phase as a catalyst support.

U.S. Pat. No. 5,985,789 discloses improved hydrogenation catalysts consisting essentially of reduced or at least partially reduced ruthenium and tin on a refractory oxide support, such as titanium oxide or zirconium oxide which is insoluble in aqueous acid. The catalysts are used for the conversion of hydrogenatable precursors, such as maleic acid, succinic acid, gamma-butyrolactone to 1,4-butanediol and gamma-butyrolactone and their mixtures. There is no disclosure of the use of titanium dioxide in the rutile crystalline phase.

M. Bankmann, R. Brand, B. H. Engler and J. Ohmer, "Forming of High Surface Area $TiO_2$ to Catalyst Supports," Catalysis Today, Vol. 14, pages 225-242 (1992), contains an extensive discussion of the use of titanium dioxide having a high surface area as a catalyst support. The article (which was previously presented in a substantially identical form by R. Brand at the Fall, 1991 American Chemical Society meeting) indicates that the titanium dioxide must have a high surface area in order to be a suitable catalyst support and discusses only titanium dioxide having surface areas of 50 and 100 square meters per gram. The article discusses the extrusion process for manufacturing titanium dioxide having the requisite high surface area and the effect of the raw materials, additives and process parameters employed in the extrusion process on catalytically important characteristics of the resulting titanium dioxide. As disclosed, the extrusion process involves the steps of: (1) mixing and kneading the raw materials, (2) extruding, (3) drying, and (4) calcining, each of which influences the quality of the resulting support. Correlations between the concentration of water, plasticizers and binders and the type of titanium dioxide raw material employed in the mixing and kneading step and the crushing strength, attrition resistance, pore diameter and pore volume of the resulting catalyst support, and correlations between the calcination temperature and the surface area, pore volume, mean pore diameter and pore size distribution and the degree of transformation from the anatase crystalline phase to the rutile crystalline phase in the resulting catalyst support, are discussed in the article. More particularly, the use of catalysts containing palladium, platinum or rhodium components supported on titanium dioxide for selective hydrogenation is disclosed. On pages 240 to 241, the use of such catalysts to hydrogenate a para-substituted benzaldehyde to the corresponding para-substituted benzyl alcohol or para-substituted toluene is disclosed. The table on page 241 indicates that the para-substituent can be a carboxylic acid group, a methyl group or a halogen. The article discloses that the results of the hydrogenation of para-substituted benzaldehyde were substantially different depending upon whether the catalyst contained palladium, platinum or rhodium on the titanium dioxide support. The article indicates that the titanium dioxide must have a high surface area in order to be a suitable catalyst support and discusses only titanium dioxide having surface area of 50 and 100 square meters per gram. In addition, the article discloses that depending on the reaction temperature employed, the reduction of a para-substituted benzaldehyde affords either of several products with high selectivity and in high yield. Except for the catalysis, the reaction temperature and the hydrogen pressure employed, the article does not disclose the conditions under which the hydrogenation was performed.

In commonly assigned U.S. Pat. No. 5,362,908, to Schroeder et al., a method employing a titanium dioxide-supported purification catalyst is disclosed for purification-by-hydrogenation of a crude terephthalic acid, crude isophthalic acid or a crude naphthalene dicarboxylic acid produced by the liquid-phase oxidation with an oxygen-containing gas in a solvent at an elevated temperature and pressure and in the presence of an oxidation catalyst comprising a heavy metal component. The purification-by-hydrogenation process according to U.S. Pat. No. 5,362,908 comprises passing an at least partially aqueous solution of crude aromatic dicarboxylic acid at a pressure sufficient to maintain the solution substantially in the liquid phase through a particulate catalyst bed in the presence of hydrogen. Particulate catalyst for this purification-by-hydrogenation process is a noble metal of Group VIII of the Periodic Table of Elements on a titanium dioxide support which does not disintegrate in less than one month under conditions employed in the hydrogenation. Preferably, at least one weight percent of the titanium dioxide support is in the rutile crystalline phase, and at least about 90 weight percent of the titanium support is, more preferably, in the rutile crystalline phase. However, even after hydrogenation, the terephthalic acid product contains color bodies.

Commonly assigned U.S. Pat. No. 5,616,792 discloses processes using a titanium dioxide-supported purification catalyst for purification of relatively impure dicarboxylic aromatic acid produced by liquid-phase oxidation of a suitable benzene or naphthalene having two oxidizable ring substituents, and/or by recovery from polyester resin comprising repeating units of the dicarboxylic aromatic acid residue and repeating units of dihydric alcohol residue. Purification comprises passing an aqueous solution of dicarboxylic aromatic acid with small amounts of organic impurities consisting of oxygen-containing aromatic co-products of oxidation and/or other organic components, through a particulate bed of purification catalyst comprising a noble metal on a titanium dioxide support under conditions suitable for decarbonylation of organic impurities. Generally, at least one weight percent of the titanium dioxide support is in the rutile crystalline phase. Optionally, effluent aqueous solution from the bed containing noble metal on the titanium dioxide support is passed through a subsequent particulate bed of another purification catalyst in the presence of a molecular hydrogen-containing gas. Hydrogenation of the aqueous solution subsequent to decarbonylation further reduces organic impurities in dicarboxylic aromatic acid recovered by crystallization and separation from the aqueous solution.

Commonly assigned U.S. Pat. No. 5,756,833 discloses processes using a titanium dioxide-supported purification catalyst for purification of relatively impure dicarboxylic aromatic acid produced by liquid-phase oxidation of a suitable benzene or naphthalene having two oxidizable ring substituents, and/or by recovery from polyester resin comprising repeating units of the dicarboxylic aromatic acid residue and repeating units of dihydric alcohol residue. Purification comprises passing an aqueous solution of dicarboxylic aromatic acid with small amounts of organic impurities consisting of oxygen-containing aromatic co-products of oxidation and/or other organic components, through a particulate bed of purification catalyst comprising a noble metal on a titanium dioxide support under conditions suitable for decarbonylation of organic impurities. Generally, at least one weight percent of the titanium dioxide support is in the rutile crystalline phase. Optionally, effluent aqueous solution from the bed containing noble metal on the titanium dioxide support is passed through a subsequent particulate bed of another purification catalyst in the presence of a molecular hydrogen-containing gas. Hydrogenation of the aqueous solution subsequent to decarbonylation further reduces organic impurities in dicarboxylic aromatic acid recovered by crystallization and separation from the aqueous solution.

Titanium dioxide which is primarily in the anatase crystalline phase also has disadvantages as a catalyst support. The anatase $TiO_2$ has a low crush strength and is also subject to disintegrating and producing particles which can clog the catalyst pores and reduce the efficiency of the reaction.

There are many areas where improvement is needed in catalysts previously used to produce BDO, GBL, and THF. Some of these are: more uniform particle length distribution, minimization of fines and chips to reduce delta P, harder particles for retarding the delta P increase due to degradation, longer life at full rate of production. It may be possible to increase production if one can reduce the bed delta P.

An object of this invention is a process and a catalyst which can maximize 1,4-butanediol production and minimize gamma-butyrolactone production. Such a catalyst would be more economical because more of the more desired BDO product would be produced and because recycling GBL increases the overall process costs.

A catalyst which does not require the use of sodium, iron, and silver, in which the amount of palladium and rhenium can be reduced, and in which carbon is replaced with a much harder, more uniform support would also be more economical and would be desirable. The present invention provides such a catalyst by using a hydrogenation catalyst comprising one or more active hydrogenation catalyst components on a catalyst support comprising titanium dioxide in the rutile crystalline phase.

The catalyst of the present invention provides the above desired features. The present invention uses a catalyst comprising a hydrogenation catalyst comprising one or more active hydrogenation catalyst components on a support comprising titanium dioxide in the rutile crystalline phase to overcome disadvantages, such as flaking, high delta P, and low crush strength, found with other catalyst supports. The catalyst of the present invention also has the advantage that less nitric acid is needed for catalyst preparation which makes use of the catalyst less adverse to the environment and more desirable where the impact on the environment is an important factor.

SUMMARY OF THE INVENTION

The present invention relates to a process for catalytically hydrogenating a hydrogenatable precursor in contact with a hydrogen-containing gas and a hydrogenation catalyst comprising one or more active hydrogenation catalyst components on a support comprising titanium dioxide in the rutile crystalline phase to produce 1,4-butanediol and, optionally, gamma-butyrolactone and/or tetrahydrofuran.

This invention also relates to a process for the hydrogenation of maleic acid to 1,4-butanediol and, optionally, gamma-butyrolactone and/or tetrahydrofuran wherein
(a) selective reduction of maleic acid to succinic acid is achieved in the first step of the hydrogenation process by using a hydrogenation catalyst component supported on titanium dioxide in the rutile form, and
(b) selective reduction of the succinic acid to produce BDO, THF, and GBL, or mixtures thereof, is achieved in the second step of the hydrogenation process by using
(i) a hydrogenation catalyst comprising one or more hydrogenation catalyst components supported on titanium dioxide in the rutile form,
(ii) a hydrogenation catalyst comprising one or more active hydrogenation catalyst components supported on carbon, or
(iii) mixtures thereof.

By using a hydrogenation catalyst comprising one or more active hydrogenation catalyst components on a rutile titanium dioxide support in the first stage reaction, it is possible to use a less expensive carbon-supported catalyst with fewer hydrogenation metals in the second stage and still obtain good BDO production. For example, it is possible to eliminate iron and sodium in a carbon-supported catalyst used in the second stage reaction and also to reduce the amount of silver in the catalyst. This reduces the overall catalyst cost.

This invention further relates to a process for the production of succinic acid or succinic anhydride by the hydrogenation of maleic acid to produce succinic acid using a hydrogenation catalyst supported on titanium dioxide in the rutile form, and then, optionally, dehydrating the succinic acid to convert the succinic acid to succinic anhydride.

The present invention additionally relates to a process for the production of succinic acid or succinic anhydride by catalytically hydrogenating a hydrogenatable precursor, selected from the group consisting of maleic acid, maleic anhydride, fumaric acid, maleate esters, and mixtures thereof in contact with a hydrogen-containing gas and a hydrogenation catalyst on a support comprising titanium dioxide in the rutile crystalline phase to produce succinic acid, and optionally dehydrating the succinic acid to product succinic anhydride.

Advantageously, the titanium dioxide support of the present invention has, at least about one weight percent of the titanium support in the rutile crystalline phase, preferably at least about 70 weight percent, more preferably at least about 75 weight percent of the titanium support in the rutile crystalline phase, more preferably at least about 77 weight percent of the titanium support in the rutile crystalline phase, more preferably at least about 80 weight percent of the titanium support in the rutile crystalline phase, more preferably at least about 83 weight percent of the titanium support in the rutile crystalline phase, more preferably at least about 85 weight percent of the titanium support in the rutile crystalline phase, more preferably at least about 90 weight percent of the titanium support in the rutile crystalline phase, more preferably at least about 94 weight percent of the titanium support in the rutile crystalline phase, more preferably at least about 95 weight percent of the titanium support in the rutile crystalline phase, more preferably at least about 97 weight percent of the titanium support in the rutile crystalline phase, more preferably at least about 98 weight percent of the titanium support in the rutile crystalline phase, more preferably at least about 99 weight percent of the titanium support in the rutile crystalline phase, and more preferably at least about 100 weight percent of the titanium support in the rutile crystalline phase.

This invention also relates to a process for catalytically hydrogenating a hydrogenatable precursor in contact with a hydrogen-containing gas and a hydrogenation catalyst on a support comprising titanium dioxide, wherein at least about 85 wt % of the titanium dioxide is in the rutile crystalline phase, to produce 1,4-butanediol and, optionally, gamma-butyrolactone and/or tetrahydrofuran.

The present invention also relates to a catalyst comprising palladium and rhenium on a support comprising titanium dioxide in the rutile crystalline phase. Preferably the support comprises at least about 1 wt %, preferably about 70 wt %, more preferably about 75 wt %, more preferably about 80 wt %; more preferably about 83 wt %; more preferably about 85 wt %, more preferably about 90 wt %, more preferably about 94 wt % more preferably about 95 wt %, more preferably about 97 wt %, more preferably about 98 wt %, more preferably about 99 wt %, and more preferably about 100 wt % of rutile titanium dioxide.

The catalyst may additionally comprise at least one of silver, iron, aluminum, cobalt, gold, manganese, tungsten, molybdenum, ruthenium, rhodium, osmium, iridium, and platinum, and mixtures thereof.

The hydrogenatable precursor is advantageously selected from the group consisting of maleic acid, maleic anhydride, fumaric acid, succinic acid, succinic anhydride, maleate esters, succinate esters, gamma-butyrolactone and mixtures thereof.

The present invention also relates to a process for the production of 1,4-butanediol comprising catalytically hydrogenating a hydrogenatable precursor in contact with a hydrogen-containing gas and a hydrogenation catalyst comprising palladium, rhenium, and at least one of silver, iron, aluminum, cobalt and mixtures thereof, on a support comprising titanium dioxide in the rutile crystalline phase.

Description of the Preferred Embodiment(s)

The present invention relates to a process for catalytically hydrogenating a hydrogenatable precursor in contact with a hydrogen-containing gas and a hydrogenation catalyst comprising one or more active hydrogenation catalyst components on a support comprising titanium dioxide in the rutile form to produce 1,4-butanediol and, optionally, gamma-butyrolactone and/or tetrahydrofuran.

This invention also relates to a process for the hydrogenation of maleic acid to 1,4-butanediol and, optionally, gamma-butyrolactone and/or tetrahydrofuran wherein selective reduction of maleic acid to succinic acid is achieved in the first step of the hydrogenation process by using a hydrogenation catalyst comprising one or more active hydrogenation catalyst components on a catalyst support comprising titanium dioxide in the rutile crystalline phase.

The hydrogenation catalyst component comprises at least one noble metal of Group VIII of the Periodic Table.

Advantageously, the noble metal of Group VIII of the Periodic Table is selected from the group consisting of palladium, ruthenium, rhodium, osmium, iridium and platinum.

In an embodiment of the invention, the hydrogenation catalyst comprises palladium on a rutile titanium dioxide support. The amount of palladium in the catalyst is from about 0.05 to about 20 wt %, preferably from about, 0.1 to about 10 wt %, about 0.5 to about 7 wt %; about 0.5 to about 5 wt %; about 0.3 to about 5 wt %; about 0.2 to about 5 wt %, or about 0.2 to about 3.0 wt % of total catalyst.

In addition to palladium, the hydrogenation catalyst may also comprise about 0.1 to about 20 wt % rhenium, preferably about 0.5 to about 15 wt % rhenium, about 1.0 to about 10 wt % rhenium, about 1.0 to about 5.0 wt % rhenium, and may additionally comprise about 0.1 to about 20 wt % silver, preferably, about 0.5 to about 10 wt % silver, preferably about, 1.0 to about 8 wt % silver, about 0.1 to about 5 wt % silver, or about 0.5 to about 4.0 wt % silver based on total catalyst weight, on a rutile titanium dioxide support.

When the catalyst is used in the first stage of a two stage process, the amount of palladium preferably is in a range of from about 0.05 wt % to about 5.0 wt %, more preferably from about 0.1 wt % to about 3.0 wt %, and more preferably from about 0.2 wt % to about 0.6 wt %, and the amount of rhenium may be from 0 wt % to about 3.0 wt %, preferably from about 0.1 wt % to about 2.9 wt %, more preferably from about 0.2 wt % to about 2.0 wt % based on total catalyst weight.

When the catalyst is used in the second stage of a two-stage process, the amount of palladium preferably is in a range of from about 0.05 wt % to about 5.0 wt %, more preferably from about 0.5 wt % to about 4.0 wt %, and more preferably from about 1.0 wt % to about 3.0 wt %, and the amount of rhenium is preferably from about 1 wt % to about 10.0%, more preferably from about 4 wt % to about 8 wt %, more preferably from about 5 wt % to about 7 wt % based total catalyst weight.

The hydrogenation catalyst may also comprise at least one noble metal of Group VIII of the Periodic Table and at least one of rhenium, tungsten and molybdenum on a rutile titanium dioxide support.

The hydrogenation catalyst may also comprise palladium, silver, rhenium and at least one of iron, aluminum, cobalt and mixtures thereof on a rutile titanium dioxide support.

In one embodiment, the hydrogenation catalyst component comprises between about 0.1 to about 20 wt % palladium, between about 0.1 to about 20 wt % silver, between about 0.1 to about 20 wt % rhenium, and between about 0.1 to about 5 wt % of at least one of iron, aluminum, cobalt and mixtures thereof on a rutile titanium dioxide support.

In another embodiment the hydrogenation catalyst comprises about 0.2 to 4 wt % palladium, about 0.5 to 4 wt % silver, about 0.5 to 10 wt % rhenium, and about 0.2 to 0.6 wt % of at least one of iron, aluminum, cobalt and mixtures thereof on a rutile titanium dioxide support.

An embodiment of the present invention also relates to catalysts comprising palladium and rhenium on a rutile titanium dioxide support which are useful for the hydrogenation of maleic anhydride, maleic acid and related compounds to tetrahydrofuran, gamma-butyrolactone and 1,4-butanediol. Rutile titanium dioxide is a titanium dioxide which has been calcined at high temperature to convert it from the anatase crystalline phase to the rutile crystalline phase.

An embodiment of the instant invention relates to hydrogenation catalysts comprising palladium, rhenium, silver, and at least one of iron, aluminum, cobalt and mixtures thereof, all on a rutile titanium dioxide support, which are useful for the hydrogenation of maleic anhydride, maleic acid and related compounds to 1,4-butanediol, tetrahydrofuran, and/or gamma-butyrolactone. The rutile titanium dioxide support of the present invention comprises at least about one wt % of titanium dioxide in the rutile crystalline phase.

Generally, at least about 70 weight percent of the titanium dioxide support of the present invention is in the rutile crystalline phase. Advantageously, the titanium dioxide support has at least about 75 weight percent of the titanium dioxide support in the rutile crystalline phase, at least about 77 weight percent of the titanium dioxide support in the rutile crystalline phase, at least about 80 weight percent of the titanium dioxide support in the rutile crystalline phase, at least about 83 weight percent of the titanium dioxide support in the rutile crystalline phase, at least about 85 weight percent of the titanium dioxide support in the rutile crystalline phase, at least about 90 weight percent of the titanium dioxide support in the rutile crystalline phase, at least about 94 weight percent of the titanium dioxide support in the rutile crystalline phase, at least about 95 weight percent of the titanium dioxide support in the rutile crystalline phase, at least about 97 weight percent of the titanium dioxide support in the rutile crystalline phase, at least about 98 weight percent of the titanium dioxide support in the rutile crystalline phase, at least about 99 weight percent of the titanium dioxide support in the rutile crystalline phase, or at least about 100 weight percent of the titanium dioxide support in the rutile crystalline phase.

The present invention relates to a hydrogenation catalyst for the conversion of maleic acid to succinic acid which can then be converted to 1,4-butanediol using the same or a different hydrogenation catalyst. The catalyst of the invention has the advantages of better crush strength, delta P, productivity, and catalyst life compared to previous hydrogenation catalyst systems. The catalyst of the present invention comprises palladium and rhenium on the rutile form of titanium dioxide. The novel catalyst of the present invention, Pd/Re on rutile $TiO_2$, can convert maleic acid to succinic acid at a very high selectivity. The succinic acid selectivity can be as high as 98%. Advantageously the succinic acid selectivity is at least about 65%, preferably at least about 75%, more preferably at least about 85%, more preferably at least about 90%, more preferably at least about 95%, and more preferably at least about 98%.

In the process of the present invention, at least about 85 wt %, preferably, about 90 wt %, more preferably about 95 wt %, more preferably about 98 wt % more preferably 99.5 wt %, and more preferably 100 wt % of maleic acid is converted to succinic acid. The succinic acid product may be recovered and used or converted via dehydration to succinic anhydride, or the succinic acid product may be converted to BDO, THF, GBL, or mixtures thereof using the same or a different hydrogenation catalyst.

The amounts of palladium and rhenium in the catalyst preferably may vary from about 0.05 to about 20.0 wt % based on total catalyst weight, more preferably about 0.1 to about 5.0 wt %. The amount of palladium is preferably about 0.05 wt % to about 5.0 wt %, preferably about 0.1 wt % to about 3 wt %.

The rutile form of titanium dioxide is much more stable to highly acidic conditions such as the concentrated (up to 50 wt %) maleic acid solution than the more commonly used anatase form of titanium dioxide. The rutile form of $TiO_2$ is harder than standard carbon and also harder than anatase $TiO_2$. Therefore, the rutile form of titanium dioxide is more suitable, desirable and beneficial for the catalyst of the present invention than the mixed or anatase form of $TiO_2$.

The catalyst of the present invention preferably comprises palladium and rhenium on a titanium dioxide support comprising at least about 1 wt % of the rutile form of titanium dioxide, preferably at least about 83 wt % of the rutile form of titanium dioxide.

The catalyst of the present invention has an advantage over catalysts which have supports of carbon. Carbon is fragile. When softer catalysts break, they close and decrease the void spaces. This blocks the flow of the reactants. It reduces the flow and builds up pressure. If the delta P increases, it slows down the reaction and fresh catalyst must be put in, which is costly. When catalyst is made with a carbon support it flakes under the reaction conditions and blocks the catalyst void spaces and causes a higher delta P. This slows down the reaction throughput and the higher delta P can crush the catalyst.

Another disadvantage of catalysts having a carbon support is that, with a carbon support, a larger amount of hydrogenation metal is needed, sodium is also needed. While it is not intended that this invention be bound or limited by any particular theory, it is believed that sodium is needed to anchor the palladium hydrogenation metal to the carbon support. With a catalyst support of titanium dioxide in the rutile crystalline phase, sodium is not necessary. With the rutile $TiO_2$ support, it may also be possible to reduce or eliminate other hydrogenation metals that are sometimes used, such as silver, thus saving on catalyst costs.

Catalyst supports made from titanium dioxide in the anatase crystalline phase are not as hard as the catalyst support of the present invention which comprises titanium dioxide wherein at least about 83 weight percent of the titanium dioxide is in the rutile crystalline phase. An anatase $TiO_2$ catalyst support can be chemically attacked by the maleic or succinic acid at the temperatures used in the reaction process. When acid attacks a $TiO_2$ catalyst in the anatase crystalline phase, it flakes off and becomes softer and breaks down which can lead to the same problems of clogging of catalyst void spaces and pressure build up as with a carbon support.

An advantage of the catalyst of the present invention is that the support comprises titanium dioxide in the rutile crystalline phase. The rutile $TiO_2$ support is harder and can survive the chemical attack caused by the acid conditions of the reaction system. Use of rutile titanium dioxide provides a great advantage in terms of hardness and chemical inertness so the catalyst lasts longer and is more economical. Use of a catalyst with a support comprising rutile titanium dioxide can lead to a cost savings in the process.

In the process of the present invention, maleic acid or other hydrogenatable precursors are hydrogenated in the presence of a noble metal catalyst to succinic acid and, optionally, to 1,4-butanediol, tetrahydrofuran and gamma-butyrolactone or mixtures thereof. The production and yields of 1,4-butanediol are enhanced by use of a catalyst support comprising titanium in the rutile crystalline phase.

Reactants

In the process of the instant invention, at least one hydrogenatable precursor is reacted with a hydrogen containing gas in the presence of the catalyst. Generally the hydrogenatable precursor is in an aqueous solution and the reaction is conducted in an aqueous reaction medium.

As used herein a "hydrogenatable precursor" is any carboxylic acid or anhydride thereof, carboxylic acid ester, lactone or mixture thereof which when hydrogenated produces 1,4-butanediol. Representative hydrogenatable precursors include maleic acid, maleic anhydride, fumaric acid, succinic anhydride, succinic acid, succinate esters such as the $C_1$ to $C_8$ dialkyl succinates (e.g. dimethyl succinate), maleate esters such as the $C_1$ to $C_8$ dialkyl maleates (e.g. dimethyl maleate), gamma-butyrolactone or mixtures thereof The preferred hydrogenatable precursors are maleic acid, maleic anhydride, succinic acid, succinic anhydride, fumaric acid, esters of $C_4$ acids, gamma butyrolactone or mixtures thereof.

If the goal is to produce succinic acid, then the preferred hydrogenatable precursors are maleic acid and maleic anhydride.

The most preferred hydrogenatable precursor is maleic acid, which is typically obtained by reacting n-butane or benzene in an oxygen-containing gas in the presence of a catalyst to oxidize in the vapor phase the n-butane or benzene to maleic anhydride, and then collecting the maleic anhydride by a water quench to produce maleic acid in an aqueous solution. The oxidation of n-butane or benzene is typically operated at a temperature of about 300° C. to 600° C. and a pressure of about 0.5 to 20 atmospheres (50 to 2000 kPa).

Typically, the hydrogen ($H_2$) containing gas is commercially pure hydrogen with no diluent gases. However, the hydrogen containing gas in addition to hydrogen ($H_2$) may also contain nitrogen ($N_2$), any gaseous hydrocarbon (e.g. methane), as well as gaseous oxides of carbon, (e.g. carbon monoxide, carbon dioxide).

The Catalyst

The catalyst employed in the instant invention comprises a noble metal of Group VIII of the Periodic Table selected from the group consisting of at least one of palladium, ruthenium, rhodium, osmium, iridium and platinum on a support comprising at least about 1 wt % rutile titanium dioxide, preferably at least about 83 wt % rutile titanium dioxide.

Catalysts used in the instant invention may also contain: (i) at least one of rhenium, manganese or tellurium; (ii) at least one of silver and gold; and (iii) at least one metal capable of alloying with the noble Group VIII metal and at least one of rhenium, tungsten or molybdenum. These catalyst composition may also be further modified through the incorporation of a metal or metals selected from Groups IA, IIA or VIII.

Preferably, the catalyst employed in the instant invention comprises palladium, or palladium and rhenium, on a rutile titanium dioxide support. Advantageously, the rutile titanium support comprises at least about 83 wt % of titanium dioxide in the rutile crystalline phase.

More preferably, the catalyst employed in the instant invention comprises palladium and rhenium on a rutile titanium dioxide support wherein the rutile titanium support comprises at least about 90 wt % of titanium dioxide in the rutile crystalline phase, more preferably at least about 95 wt % of titanium dioxide in the rutile crystalline phase.

Preferably the catalyst composition comprises about 0.01 to about 20 weight percent palladium, preferably about 0.05 to about 8 weight percent palladium, about 0.1 to about 5 weight percent palladium, or about 0.2 to about 3 weight percent palladium. When rhenium is a catalyst component, the catalyst additionally comprises about 0.1 to about 20 weight percent rhenium, preferably about 0.1 to about 15 weight percent rhenium, about 0.5 to about 10 weight percent rhenium, about 0.5 to about 7 weight percent rhenium, or about 0.5 to about 4.0 weight percent rhenium.

Another catalyst which may be employed in the instant invention comprises palladium, rhenium, and silver supported on rutile titanium dioxide. Advantageously, the rutile titanium support comprises at least about 1%, and preferably at least about 83 wt % of titanium dioxide in the rutile crystalline phase.

The Pd/Re/Ag catalyst composition can comprise about 0.05 to about 20 weight percent palladium, preferably about 0.1 to about 8 weight percent palladium; more preferably about 0.2 to about 4 weight percent palladium; about 0.1 to about 20 weight percent rhenium, preferably about 1 to about 5 weight percent rhenium; and about 0.1 to about 20 weight percent silver, preferably about 0.5 to about 8 weight percent silver, preferably about 1 to about 5 weight percent silver. The ratio of palladium to silver is between 10 to 1 and 1 to 10. This catalyst composition may also be further modified through the incorporation of a metal or metals selected from Groups IA or IIA.

The preferred catalysts for use in this invention may be conveniently prepared by impregnation of the rutile titanium dioxide support, either in single or multiple impregnation steps, with a solution or solutions containing at least one palladium, silver, or rhenium compound. As used herein, impregnation of the rutile titanium dioxide support means to cause the rutile titanium dioxide support to be filled, imbued, permeated, saturated or coated. The impregnating solution may optionally contain complexing agents to help solubilize one or more of the metal compounds. The catalyst is dried after each impregnation step to remove any carrier solvent. Drying temperatures are between about 80° C. and about 150° C. Optionally, the hydrogenation catalyst may then be calcined at about 150° C. to about 350° C.

In making the preferred catalysts, the solutions of palladium compound, silver compound and rhenium compound can be applied to the rutile titanium dioxide by immersing or suspending the support material in the solution or by spraying the solution onto the titanium dioxide, or by precipitating the hydrogenation catalyst components onto the titanium dioxide.

A procedure which can be used for edge-coating the titanium dioxide support with hydrogenation catalyst components is described in Che, M.; Clause, O.; and Marcilly, Ch., "Impregnation and Ion Exchange" Handbook of Heterogeneous Catalysis, Volume 1, pages 191-207, Edited by: G. Ertl, H. Knozinger, J. Weitkamp, ISPN: 352729212-8, (1997 Edition), incorporated herein by reference in its entirety.

The solution containing the palladium compound is typically an aqueous solution containing an amount of palladium compound to yield a catalyst product with the requisite amount of palladium. The palladium compound may be palladium nitrate or a palladium compound such as a chloride, carbonate, carboxylate, acetate, acetyl acetonate, or amine. The solution containing the silver compound is typically an aqueous one containing an amount of silver compound to yield a catalyst product with the requisite amount of silver. The palladium and silver compounds should be thermally decomposable and reducible to the metals. The solution containing the rhenium compound is typically an aqueous one containing an amount of rhenium compound to yield a catalyst product with the requisite amount of rhenium. The rhenium compound is typically perrhenic acid, ammonium perrhenate or an alkali metal perrhenate.

The impregnating solution(s) may optionally contain metal complexing agents to help solubilize one or more of the metal compounds. The addition of acetonitrile to the impregnating solution allows the Pd, Re, and Ag compounds to be added in a single step. Nitric acid may also be added to the impregnating solution.

After impregnation with palladium, silver, and rhenium and drying, the preferred catalyst is activated by heating the impregnated rutile titanium dioxide support under reducing conditions at a temperature of about 120° C. to about 350° C., preferably about 150° C. to about 300° C. Hydrogen, or a mixture of hydrogen and nitrogen, in contact with the catalyst may be conveniently used for the catalyst reduction. Reduction of the impregnated rutile titanium dioxide support is only after the rutile titanium dioxide support has been impregnated with palladium, silver, and rhenium. In the case of multiple impregnation steps and multiple dryings, the reduction of the catalyst is done after the final drying.

The Process

The method for carrying out the process comprises reacting a hydrogenatable precursor with a hydrogen-containing gas in the presence of the hydrogenation catalyst, and recovering and purifying the reaction products, typically by distillation.

The liquid phase hydrogenation of this invention can be run using conventional apparatus and techniques in a stirred-tank reactor or in a fixed-bed reactor. Single or multiple-stage reactors may be employed. The amount of catalyst required will vary widely and is dependent upon a number of factors such as reactor size and design, contact time and the like.

The hydrogen-containing gas is fed continuously, generally with the hydrogen in considerable stoichiometric excess to the other reactants. Unreacted hydrogen can be returned to the reactor as a recycle stream. The precursor solution, e.g., maleic acid (or other hydrogenatable precursor) solution, is fed continuously at concentrations ranging from dilute solutions to near the maximum solubility level. The precursor solution may contain about 10 to about 60 weight percent maleic acid (or other hydrogenatable precursor) with the higher concentrations being more economical and preferred due to less water to recycle or dispose. Preferably the precursor solution contains about 20 to about 40 weight percent maleic acid (or other hydrogenatable precursor).

Advantageously, the hydrogenation is run at a temperature of from about 50° C. to about 350° C., preferably from about 50° C. to about 250° C. and a hydrogen pressure of from about 20 to about 400 atmospheres (about 294 psig to about 5878 psig) with hydrogen to hydrogenatable precursor ratios ($H_2$/P) of between 5 to 1 and 1000 to 1 and contact times of from about 0.1 minute to about 20 hours.

The reaction products, 1,4-butanediol, tetrahydrofuran, gamma-butyrolactone or mixtures thereof, are advantageously separated by fractional distillation. By-products which are formed in small amounts or unreacted feed, such as, for example, succinic anhydride or succinic acid, are optionally returned to the hydrogenation stage. The gamma-butyrolactone may also be recycled to the hydrogenation reactor.

Using the process of this invention, more specifically using the hydrogenation catalyst described herein, maleic acid is converted virtually quantitatively in a simple reaction. The yields of 1,4-butanediol and tetrahydrofuran achieved are about 80 mole percent or greater, typically about 90 mole percent or greater, with a majority portion of the yield being 1,4-butanediol. Reaction by-products may include n-butanol, n-butyric acid, n-propanol, propionic acid, methane, propane, n-butane, carbon monoxide, and carbon dioxide.

In an embodiment of the invention the conversion of maleic acid to 1,4-butanediol may be conducted in two separate reaction stages or hydrogenation zones In the first stage an aqueous solution of maleic acid is hydrogenated to succinic acid using a hydrogenation catalyst on a rutile titanium dioxide support, and in the second stage, the succinic acid is transported to the second reactor and further hydrogenated to 1,4-butanediol, gamma-butyrolactone, and/or tetrahydrofuran, or mixtures thereof. The catalyst used in the second reactor may be a hydrogenation catalyst on a rutile titanium dioxide support as in the first stage reaction or it may be a hydrogenation catalyst on a carbon support, such as catalysts described in U.S. Pat. No. 5,473,086; U.S. Pat. No. 5,969,164; U.S. Pat. No. 6,486,367; and U.S. Pat. No. 5,698,749 each of which is incorporated herein by reference in its entirety. For example, a catalyst used in the second stage might comprise Pd, Pd/Re, or Pd/Re/Ag on a carbon support. The catalyst might also contain one or more additional metals, such as iron. The catalyst used in the second stage may also comprise a mixture of a hydrogenation catalyst on a rutile titanium dioxide support with a hydrogenation catalyst on a carbon support.

In one embodiment, both the catalyst in the first stage and the catalyst in the second stage may comprise a mixture of a hydrogenation catalyst on a rutile titanium dioxide support with a hydrogenation catalyst on a carbon support.

Advantageously, the temperature in the first stage is from about 50° C. to about 130° C. and the temperature in the second stage is from about 100° C. to about 300° C.

In an embodiment of the above two-stage process, the temperature of the feedstream comprising maleic acid and the temperature of the first hydrogenation zone are controlled such that the temperature of maleic acid in the feedstream and the first hydrogenation zone does not exceed about 120° C., and heat is added to the reaction product from the first hydrogenation zone to raise the reaction product to a temperature of about 130° C. to about 180° C. prior to supplying the reaction product from the first hydrogenation zone to the second hydrogenation zone.

The conversion of maleic acid to 1,4-butanediol may also be conducted in two separately distinct reaction stages or zones, wherein the first stage is operated at a temperature below about 130° C., preferably below about 120° C. to convert the maleic acid to succinic acid and then the temperature of the second stage is operated at a temperature above about 130° C. to convert the succinic acid to at least one of gamma-butyrolactone, 1,4-butanediol and tetrahydrofuran. More specifically, maleic acid is supplied to a first hydrogenation zone at a temperature of about 70° C. to about 120° C. and is then hydrogenated to succinic acid. The reaction temperature in the first hydrogenation zone is controlled such that the effluent from the first hydrogenation zone does not exceed a temperature of about 130° C. Preferably, inlet and reactor temperatures are controlled in the first hydrogenation zone such that the maleic acid does not exceed about 120° C., more preferably such that the maleic acid does not exceed 100° C. The succinic acid from the first hydrogenation zone is then routed to the second hydrogenation zone at a temperature of 130° C. to about 180° C. (heat is added to this stream, if necessary) where it is hydrogenated in the second hydrogenation zone to at least one of gamma-butyrolactone, 1,4-butanediol and tetrahydrofuran. Since maleic acid is not present in a reactor at elevated temperatures (ideally no maleic acid at approximately 100° C. and above), the corrosive effects of the maleic acid are significantly minimized, thereby prolonging the life of the hydrogenation reactor(s) and any other affected process equipment and improving the overall process economics (capital, operating and maintenance costs). In this process, a catalyst comprising a hydrogenation catalyst component of the present invention on rutile $TiO_2$ would be used to convert maleic acid to succinic acid in the first hydrogenation zone and the hydrogenation catalyst used in the second hydrogenation zone to convert succinic acid to at least one of gamma-butyrolactone, 1,4-butanediol and tetrahydrofuran, could comprise a hydrogenation catalyst component on a rutile $TiO_2$ support or it could comprise a hydrogenation catalyst component on a carbon support as described above, or a mixture thereof.

Typically titanium dioxide is 100% in the anatase crystalline phase. Titanium dioxide which is in the anatase crystalline phase can be calcined to convert it to the rutile phase for use as the catalyst support as described in U.S. Pat. No. 5,362,908; U.S. Pat. No. 5,354,898; U.S. Pat. No. 5,616,792; U.S. Pat. No. 5,756,833, each of which is incorporated herein by reference in its entirety.

The support of the catalyst employed in the process of the present invention is titanium dioxide support which does not disintegrate in less than one month under the corrosive conditions that prevail in the hydrogenation of maleic acid. Such corrosive conditions are an at least partially, and preferably substantially, aqueous solution of from about 5 to about 50 weight percent of the maleic acid being hydrogenated and a hydrogenation temperature of from about 50° C. to about 350° C. The support is formed by an extrusion technique in any convenient form that can be used in a packed bed.

In one preferred embodiment, at least about 83 weight percent, preferably at least about 90 weight percent, more preferably at least about 95 weight percent, more preferably at least about 97 weight percent, and more preferably 100 weight percent of the titanium dioxide support is in the rutile crystalline phase.

Titanium dioxide which is in the anatase crystalline phase can be calcined to convert it to the rutile phase for use as the catalyst support. In a preferred embodiment the titanium dioxide support is formed by calcination of titanium dioxide at a temperature in the range of from about 600° C., preferably from about 800° C., and more preferably from about 900° C., to about 1200° C., preferably to about 1100° C., and more preferably to about 1000° C. In this embodiment, preferably at least 5 weight percent, more preferably at least 70 weight percent, more preferably at least 90 weight percent and most preferably substantially 100 weight percent, of the titanium dioxide which is calcined is initially in the anatase crystal phase.

In a further preferred embodiment, the titanium dioxide support has a total specific surface area of preferably less than about 40 square meters per gram, more preferably less than about 20 square meters per gram, and more preferably less than about 10 square meters per gram. Titanium dioxide supports having a surface area of from about 3 to about 6 square meters per gram are advantageous.

In another preferred embodiment, the titanium dioxide support has an average pore diameter of at least about 10 nanometers (nm), preferably at least about 20 nm.

In an especially preferred embodiment, at least one weight percent of the titanium dioxide support is in the rutile crystalline phase whose support contains less than 500 parts per million by weight of a sulfur-containing component, calculated as elemental sulfur, has a total specific surface area of less than about 40 square meters per gram, has an average pore diameter of at least about 10 nm, and is formed by calcination at a temperature of from about 600° C. to about 1200° C. of titanium dioxide of which at least 50 weight percent is in the anatase crystal phase.

The hydrogenation catalyst of the present invention having a support comprising at least about 83 weight percent titanium dioxide in the rutile crystalline phase has the following advantages:

a) the rutile crystalline phase titanium dioxide support is significantly harder than supports of carbon;

b) the support comprising titanium dioxide in the rutile crystalline phase is much harder than any other forms of titanium dioxide, such as catalyst supports of titanium dioxide in the anatase crystalline phase;

c) with a catalyst support comprising titanium dioxide in the rutile crystalline phase, co-catalysts or promoters such as Ag, Fe, and Na can be avoided or reduced;

d) the amount of nitric acid need to make the rutile $TiO_2$ catalyst is greatly reduced, making the catalyst production milder and more environmentally friendly;

e) the rutile $TiO_2$ catalyst preparation procedure may require fewer steps than catalysts having a carbon support (1 step, or optionally 2 steps, vs. 2 to 4 steps for carbon supports; one drying vs. several dryings for carbon supports);

f) the rutile $TiO_2$ catalyst can be used in both ⅛" (3.0 mm) or 1/16 inch (1.5 mm) catalyst diameters, whereas 1.5 mm or 1.8 mm catalyst diameter is typically preferred for catalysts with a carbon support;

g) the rutile $TiO_2$ catalyst generates few or no fines or chips during operation h) the rutile $TiO_2$ catalyst generates few or no chips during catalyst manufacturing, whereas catalysts with carbon supports generate about 1 % fines and 15% chips during catalyst manufacture;

i) the rutile $TiO_2$ catalyst has a more uniform particle length;

j) the rutile $TiO_2$ catalyst has a much longer expected life at a higher production rate than catalysts using carbon or anatase $TiO_2$ as the support; and k) the rutile $TiO_2$ has a greater crush strength than anatase $TiO_2$.

l) the rutile form of $TiO_2$ is much more stable to highly acidic conditions such as the concentrated (up to 50%) maleic acid solution than the anatase form of $TiO_2$.

m) the rutile crystalline phase titanium dioxide support has a very low sulfur content. A low sulfur content is desirable because sulfur can poison some catalysts and reduce their activity, therefore a catalyst support, such as rutile $TlO_2$, which has little or no sulfur, is advantageous.

While not intending to be bound by theory, it is believed that with rutile $TiO_2$, when it is calcined at high temperature, it begins to form some defect structures and creates a $Ti^{+3}$ structure. The term "defect" is used in X-ray terms—it means it is not perfect. $Ti^{+3}$ may bond with the rhenium and palladium. Another Ti believed to be formed in the rutile $TiO_2$ is $Ti^{+4}$. Our X-ray, electron microscopy and X-ray diffraction (XRD) data show that palladium and rhenium are well dispersed beyond the capability of dispersal in carbon or other non-rutile $TiO_2$ compositions.

Liquid hourly space velocity (liters of maleic acid solution per liter of catalyst per hour) of the aqueous crude maleic acid solution through the catalyst bed is about 0.4 $hr^{-1}$ to about 5.0 $hr^{-1}$, preferably about 0.60 $hr^{-1}$ to about 3.5 $hr^{-1}$, preferably about 0.75 $hr^{-1}$ to about 3.5 $hr^{-1}$

EXAMPLES OF THE INVENTION

It is to be understood that the subject invention is not to be limited by the examples set forth herein. These have been provided merely to demonstrate operability, and the selection of catalysts, metal sources, carbon supports, concentrations, contact times, solids loadings, feedstocks, reaction conditions, and products, if any, can be determined from the total specification disclosure provided, without departing from the spirit of the invention herein disclosed and described, the scope of the invention including modifications and variations that fall within the scope of the attached claims.

Catalyst Preparation

Carbon Catalyst A—Aqueous Three-Step Preparation of BDO Catalyst with 1.8 mm Carbon Support
Nominal Composition: 0.4% Fe, 1.9% Na, 2.66% Ag, 2.66% Pd, 10.0% Re on 1.8 mm diameter carbon.
Materials:
(A) Carbon Support:
  27.89 g of Engelhard 1.8 mm diameter active carbon available from Engelhard Corporation, Newark, N.J.
(B) Ag/Fe/Na Impregnation Solution:
  1.36 g of silver nitrate, 2.34 g of sodium nitrate and 0.96 g of [Fe $(NO_3)_3$.$9H_2O$] are dissolved in 8.19 g of de-ionized water and then gradually mixed with 17.27 g of concentrated nitric acid (70 wt % nitric acid).
(C) Pd/Re Impregnation Solution:
  A solution of 9.68 g of Pd $(NO_3)_2$(8.95% Pd) is mixed with a solution of 6.40 g of $HReO_4$(52.10 wt % Re), 12.95 g of concentrated nitric acid (70 wt % nitric acid), and 1.09 g of de-ionized water.
(D) HNO3/H2O Impregnation Solution:
  12.95 g of concentrated nitric acid (70 wt % nitric acid) and 17.17 g of de-ionized water are mixed together.
Preparation Procedure:
Step 1
  The carbon support (A) is impregnated with the Ag/Fe/Na solution (B), and allowed to stand for 1 hr. The material is then dried in an oven at 130° C. for 4.5 hr.
Step 2
  The carbon support (A) which has been impregnated with Ag/Fe/Na is next gradually impregnated with the Pd/Re impregnation solution (C) and the mixture is allowed to tumble for 1 hr then to stand for 3 hrs. The catalyst is then dried for 5 hrs at 130° C.
Step 3
  The carbon support (A) which has been impregnated with Ag/Fe/Na and Pd/Re is next gradually impregnated with the HNO3/H2O Impregnation solution (D) and the mixture is allowed to stand for 1 hr. The catalyst is then dried at 130° C. for 5 hours.
Carbon Catalyst B—Aqueous Two-Step Preparation of BDO Catalyst with 1.5 mm Carbon Support
  This procedure describes an aqueous two-step BDO catalyst preparation using Norit 1.5 mm carbon. Nominal Composition: 0.4% Fe, 1.9% Na, 2.66% Ag, 2.66% Pd, 10.0% Re on 1.5 mm diameter carbon.
Materials:
(A) Carbon Support:
  58.4 g of Norit 1.5 mm diameter Active Carbon extrudate (referred to herein as Standard C or standard carbon) (acquired from Norit Americas Inc. located in Atlanta, Ga.)
(B) Ag/Fe/Na Impregnation Solution:
  2.9 g of silver nitrate, 5.1 g of sodium nitrate and 2 g of [Fe $(NO_3)_3$.$9H_2O$] are dissolved in 20 g of de-ionized water and then gradually mixed with 68.3 g of concentrated nitric acid (70 wt % nitric acid).

(C) Pd/Re Impregnation Solution 1:
  9.1 g of Pd $(NO_3)_2$ solution (20.38% Pd), 12.22 g of $HReO_4$ solution (56.36 wt % Re), 23.3 g of concentrated nitric acid (70 wt % nitric acid), and 24 g of de-ionized water are mixed together.
Preparation Procedure:
Step 1
  The carbon support (A) is gradually impregnated with the Ag/Fe/Na impregnation solution (B), and allowed to stand for 1 hr. The material is then dried in an oven at 130° C. for 4.5 hr.
Step 2
  The carbon support (A) which has been impregnated with Ag/Fe/Na is next gradually impregnated with the Pd/Re solution (C) and the mixture is allowed to stand for 3 hr. The catalyst is then dried for 5 hr at 130° C.
Carbon Catalyst C—Aqueous Two-Step Preparation of BDO Half Metal Catalyst with Norit 1.5 mm Carbon Support
  Carbon Catalyst C has about half the amount of palladium, rhenium and silver hydrogenation metals on the carbon support as Carbon Catalyst B. Nominal Composition: 0.4% Fe, 1.9% Na, 1.33% Ag, 1.33% Pd, 5.0% Re on 1.5 mm diameter carbon support.
Materials:
(A) Carbon Support:
  58.4 g of Norit 1.5 mm diameter active carbon extrudate (Standard carbon).
(B) Ag/Fe/Na Impregnation Solution:
  1.45 g of silver nitrate, 5.1 g of sodium nitrate and 2 g of [Fe $(NO_3)_3$.$9H_2O$] are dissolved in 20 g of de-ionized water and then gradually mixed with 68.3 g of concentrated nitric acid (70 wt % nitric acid).
(C) Pd/Re Impregnation Solution 1:
  4.55 g of Pd $(NO_3)_2$ Solution (20.38% Pd)
  6.1 g of $HReO_4$ solution (56.36 wt % Re), 25.6 g of concentrated nitric acid (70 wt % nitric acid), and 27 g of de-ionized water are mixed together.
Preparation Procedure:
Step 1
  The carbon support (A) is gradually impregnated with the Ag/Fe/Na impregnation solution (B), and allowed to stand for 1 hr. The material is then dried in an oven at 130° C. for 6 hr.
Step 2
  The carbon support (A) which has been impregnated with Ag/Fe/Na is next gradually impregnated with the Pd/Re solution (C) and the mixture is allowed to stand for 3 hr. The catalyst is then dried for 5 hrs at 130° C.

Example 1(a)

0.5% Pd/2.0% Re on 1/16" Rutile Titanium Dioxide Support

Catalyst Preparation
Materials:
Rutile $TiO_2$ Support (98 wt % Rutile Crystalline Phase, 2 wt % Anatase Crystalline Phase, 1/16 inch (1.5 mm) diameter)
  Titanium dioxide containing 98 wt % of the rutile crystalline phase of titanium dioxide and 2 wt % of the anatase crystalline phase of titanium dioxide, 47.5 g (dry).
Pd/Re Impregnation Solution
  1.31 g of Pd $(NO_3)_2$ Solution (19.02 wt % Pd), 1.92 g of $HReO_4$ solution (52.1 wt % Re), and 3.93 g concentrated nitric acid (70% nitric acid) are mixed together This solution is used to impregnate the 98% rutile titanium dioxide support.

Preparation Procedure:
Step 1

The rutile titanium dioxide support is gradually impregnated with the above solution, and allowed to stand for 1 hr. The material is then dried in an oven at 130° C. for 3.5 hr.

Example 1(b)

0.5% Pd/2.0% Re on 1/8" Rutile Titanium Dioxide Support Catalyst Preparation The catalyst of Example 1(b) is made by the same procedure as the catalyst of Example 1(a) except that a rutile $TiO_2$ support comprising 98 wt % rutile crystalline phase, 2 wt % anatase crystalline phase, and having a 1/8 inch (3.0 mm) diameter is used.

Example 2

0.5% Pd on 1/8" Rutile Catalyst Preparation

An edge-coated catalyst having 0.5% Pd on 1/8" rutile $TiO_2$ support (97% Rutile, 3% Anatase, 1/8 inch diameter) was prepared by Engelhard Corporation, 101 Wood Avenue, Iselin, N.J. 08830-0770 using a procedure described in Che, M.; Clause, O.; and Marcilly, Ch.; "Impregnation and Ion Exchange" Handbook of Heterogeneous Catalysis, Volume 1, pages 191-207, Edited by: G. Ertl, H. Knozinger, J. Weitkamp, ISPN: 352729212-8, (1997 Edition).

Example 3

0.5% Pd on 1/8" Rutile Catalyst Preparation

Materials:
Rutile $TiO_2$ Support (98% Rutile, 2% Anatase 1/8 inch (3.0 mm) diameter)
Titanium dioxide containing 98 wt % of the rutile crystalline phase of titanium dioxide and 2 wt % of the anatase crystalline phase of titanium dioxide, 49.5 g (dry).
Pd Impregnation Solution
1.31 g of $Pd(NO_3)_2$ Solution (19.02 wt % Pd) is mixed with 6.12 g concentrated nitric acid (70% nitric acid). This solution is used to impregnate the 98% rutile titanium dioxide support.
Preparation Procedure:
Step 1

The 98% rutile titanium dioxide support is gradually impregnated with the Pd impregnation solution, and allowed to stand for 1 hr. The material is then dried in an oven at 130° C. for 3.5 hr.
Activity Evaluation of Catalysts The catalyst testing unit is comprised of a two-reactor system connected in series where maleic acid is first converted to succinic acid (SAC) in the first reactor at about 110° C. The effluent from the first stage reactor is delivered to the second stage reactor for the conversion of succinic acid to mainly BDO. Operating pressure is at 2500 to 4000 psi and internal reactor temperature is initially set at 165° C. Thereafter, temperature is adjusted closer to the temperature where a high conversion of SAC (about 99.7%) is obtained. This temperature generally may vary from about 130° C. to about 175° C. At the lower end of the temperature range BDO selectivity is higher (80% or higher) whereas THF is favored at higher temperatures (over 5%).

The results of the activity evaluation of a catalysts made according to the procedure of catalyst Example 1(a) is shown in Table 1a. Activity evaluation of a catalyst made according to the procedure of catalyst Example 2 is shown in Table 1(b). Catalyst results of the activity evaluation of a catalysts made according to the procedure of catalyst Example 3 is shown in Table 1(c).

TABLE 1a

Conversion of Maleic Acid (MAC) to Succinic Acid (SAC) with Catalyst Example 1(a) (0.5% Pd/2% Re on 1/16" Rutile $TiO_2$) and Conversion of SAC from the 1st stage reaction to BDO, GBL, and THF with a Standard Carbon Catalyst B (0.4% Fe, 1.9% Na, 2.66% Ag, 2.66% Pd, 10.0% Re on 1.5 mm carbon support).

| | 1st Stage Reaction | | 2nd Stage Reaction |
| | Composition | | |
| | Catalyst Example 1(a) - 0.5% Pd/2% Re on Rutile $TiO_2$ Support (98% Rutile, 2% Anatase, 1/16 inch diameter) | | Standard Carbon Catalyst B - 0.4% Fe, 1.9% Na, 2.66% Ag, 2.66% Pd, 10.0% Re on |
| Results | Mole % | Wt % | 1.5 mm carbon support |
| --- | --- | --- | --- |
| acetic acid | 0.14% | 0.08% | |
| acrylic acid | 0.00% | 0.00% | |
| 1,4-butanediol | 1.97% | 1.55% | 85.51 wt % |
| 1-butanol | 0.00% | 0.00% | |
| g-butyrolactone | 6.35% | 4.78% | 2.04 wt % |
| fumaric acid | 0.00% | 0.00% | |
| 4-hydroxybutyric acid | 1.36% | 1.24% | |
| maleic acid | 0.00% | 0.00% | |
| malic acid | 0.41% | 0.48% | |
| methanol | 0.00% | 0.00% | |
| 1,3-propanediol | 0.00% | 0.00% | |
| propionic acid | 0.00% | 0.00% | |
| succinic acid | 87.75% | 90.60% | |
| terephthalic acid | 0.00% | 0.00% | |
| THF | 2.02% | 1.27% | 9.28 wt % |
| BDO + GBL + THF | | | 96.8 wt % |
| Time on Stream | 1009 hrs. | | 1009 hrs. |
| Liquid Hourly Space Velocity | 1.6 | | 0.8 |
| MAC Conversion, % | 100 | | n.a. |
| SAC selectivity | | 90.60% | |

TABLE 1b

Conversion of Maleic Acid (MAC) to Succinic Acid (SAC) with Catalyst Example 2 (0.5% Pd on 1/8 Rutile $TiO_2$ Support (97% Rutile, 3% Anatase 1/8 inch diameter)

| | 1st Stage Reaction | | 2nd Stage Reaction |
| | Composition | | |
| | Catalyst Example 2 - 0.5% Pd on 1/8" Rutile $TiO_2$ Support (97% Rutile, 3% Anatase, 1/8 inch diameter) | | Catalyst Example 5(b) - 0.5% Pd, 5% Re on 1/16" Rutile $TiO_2$ Support (98% Rutile, 2% Anatase, 1/16 inch diameter) |
| Results | Mole % | Wt % | diameter) |
| --- | --- | --- | --- |
| acetic acid | 0.16% | 0.08% | |
| acrylic acid | 0.00% | 0.00% | |
| 1,4-butanediol | 0.49% | 0.37% | 37.81 wt % |
| 1-butanol | 0.00% | 0.00% | |
| g-butyrolactone | 0.39% | 0.28% | 52.55 wt % |
| fumaric acid | 0.00% | 0.00% | |
| 4-hydroxybutyric acid | 0.00% | 0.00% | |
| maleic acid | 0.00% | 0.00% | |
| malic acid | 0.00% | 0.00% | |
| methanol | 0.00% | 0.00% | |
| 1,3-propanediol | 0.00% | 0.00% | |

TABLE 1b-continued

Conversion of Maleic Acid (MAC) to Succinic Acid (SAC) with Catalyst Example 2 (0.5% Pd on ⅛ Rutile TiO₂ Support (97% Rutile, 3% Anatase ⅛ inch diameter)

| | 1st Stage Reaction | | 2nd Stage Reaction |
|---|---|---|---|
| | Composition | | |
| | Catalyst Example 2 - 0.5% Pd on ⅛" Rutile TiO₂ Support (97% Rutile, 3% Anatase, ⅛ inch diameter) | | Catalyst Example 5(b) - 0.5% Pd, 5% Re on 1/16" Rutile TiO₂ Support (98% Rutile, 2% Anatase, 1/16 inch diameter) |
| Results | Mole % | Wt % | |
| propionic acid | 0.00% | 0.00% | |
| succinic acid | 98.36% | 98.89% | |
| terephthalic acid | 0.00% | 0.00% | |
| THF | 0.61% | 0.37% | 2.46 wt % |
| BDO + GBL + THF | | | 92.8 wt % |
| Time on Stream | 140 hrs | | 135 hrs |
| Liquid Hourly Space Velocity | 1.6 | | 0.8 |
| MAC Conversion, % | 100 | | n.a. |
| SAC selectivity | | 98.89% | |

TABLE 1c

Conversion of Maleic Acid (MAC) to Succinic Acid (SAC) with a Catalyst Example 3 (0.5% Pd on ⅛ Rutile TiO₂ Support (97% Rutile, 3% Anatase ⅛ inch diameter)

| | 1st Stage Reaction | | 2nd Stage Reaction |
|---|---|---|---|
| | Composition | | |
| | Catalyst Example 3 - 0.5% Pd on Rutile TiO₂ Support (98% Rutile, 2% Anatase, ⅛ inch diameter) | | Standard Carbon Catalyst B - 0.4% Fe, 1.9% Na, 2.66% Ag, 2.66% Pd, 10.0% Re on 1.5 mm carbon support |
| Results | Mole % | Wt % | |
| acetic acid | 0.07% | 0.04% | |
| acrylic acid | 0.00% | 0.00% | |
| 1,4-butanediol | 0.28% | 0.21% | 90.91 wt % |
| 1-butanol | 0.12% | 0.08% | |
| g-butyrolactone | 0.08% | 0.06% | 2.51 wt % |
| fumaric acid | 0.00% | 0.00% | |
| 4-hydroxybutyric acid | 0.00% | 0.00% | |

TABLE 1c-continued

Conversion of Maleic Acid (MAC) to Succinic Acid (SAC) with a Catalyst Example 3 (0.5% Pd on ⅛ Rutile TiO₂ Support (97% Rutile, 3% Anatase ⅛ inch diameter)

| | 1st Stage Reaction | | 2nd Stage Reaction |
|---|---|---|---|
| | Composition | | |
| | Catalyst Example 3 - 0.5% Pd on Rutile TiO₂ Support (98% Rutile, 2% Anatase, ⅛ inch diameter) | | Standard Carbon Catalyst B - 0.4% Fe, 1.9% Na, 2.66% Ag, 2.66% Pd, 10.0% Re on 1.5 mm carbon support |
| Results | Mole % | Wt % | |
| maleic acid | 0.06% | 0.06% | |
| malic acid | 0.32% | 0.36% | |
| methanol | 0.02% | 0.00% | |
| 1,3-propanediol | 0.00% | 0.00% | |
| propionic acid | 0.00% | 0.00% | |
| succinic acid | 98.31% | 98.73% | |
| terephthalic acid | 0.00% | 0.00% | |
| THF | 0.74% | 0.45% | 2.92 wt % |
| BDO + GBL + THF | | | 96.3 wt % |
| Time on Stream | 193 hrs | | @209 hrs. |
| Liquid Hourly Space Velocity | 1.6 | | 0.8 |
| MAC Conversion, % | 100 | | n.a. |
| SAC selectivity | | 98.73% | |

Tables 1a, 1b and 1c show that catalysts of Example 1(a), comprising Pd/Re on a rutile titanium dioxide support, and catalysts of Example 2 and Example 3, comprising Pd on a rutile titanium dioxide support, completely convert maleic acid to succinic acid with high selectivity to succinic acid and low amounts of other by-products.

The Catalyst Testing Unit (CTU) results for Catalyst Example 1 and Catalyst Example 2 show that (a) Both 1/16 inch and ⅛ inch Rutile extrudates can be used for hydrogenation. For carbon, ⅛ inch was found to be less effective.

(b) For maleic to succinic hydrogenation there is no need for other co-catalysts such as Ag, Fe, Na, etc., (c) 0.5% Pd alone on a rutile TiO₂ support gives good conversion of maleic acid to succinic acid.

Tables 2a and 2b show the results of hydrogenation of maleic acid to succinic acid over several sample time periods using catalysts prepared as described in Catalyst Example 1(a) and Catalyst Example 2.

TABLE 2a

Hydrogenation Results Using Rutile TiO₂ 1/16" Support and Pd/Re Catalyst (Catalyst Example 1(a) - 0.5% Pd/2.0% Re on 1/16" Rutile Titanium Dioxide Support, 98% Rutile/2% Anatase) to convert Maleic Acid to Succinic Acid

| | Rutile 1, 1/16" | | | | | |
|---|---|---|---|---|---|---|
| | Time on Stream (TOS), hrs | | | | | |
| | 170 | | 241 | | 380 | |
| | Mole % | Wt % | Mole % | Wt % | Mole % | Wt % |
| acetic acid | 0.12% | 0.06% | 0.14% | 0.07% | 0.07% | 0.04% |
| acrylic acid | 0.00% | 0.00% | 0.00% | 0.00% | 0.00% | 0.00% |
| 1,4-butanediol | 0.35% | 0.28% | 1.54% | 1.22% | 0.39% | 0.31% |
| 1-butanol | 0.10% | 0.06% | 0.21% | 0.14% | 0.00% | 0.00% |
| g-butyrolactone | 7.98% | 6.01% | 7.90% | 5.97% | 7.68% | 5.77% |
| fumaric acid | 0.10% | 0.11% | 0.00% | 0.00% | 0.00% | 0.00% |
| 4-hydroxybutyric acid | 1.74% | 1.58% | 2.95% | 2.70% | 1.59% | 1.44% |

TABLE 2a-continued

Hydrogenation Results Using Rutile TiO$_2$ 1/16" Support and Pd/Re Catalyst (Catalyst Example 1(a) - 0.5% Pd/2.0% Re on 1/16" Rutile Titanium Dioxide Support, 98% Rutile/2% Anatase) to convert Maleic Acid to Succinic Acid

| | | | | | | |
|---|---|---|---|---|---|---|
| maleic acid | 0.00% | 0.00% | 0.04% | 0.04% | 0.00% | 0.00% |
| malic acid | 0.15% | 0.18% | 0.29% | 0.34% | 0.00% | 0.00% |
| methanol | 0.00% | 0.00% | 0.00% | 0.00% | 0.00% | 0.00% |
| 1,3-propanediol | 0.00% | 0.00% | 0.00% | 0.00% | 0.00% | 0.00% |
| propionic acid | 0.00% | 0.00% | 0.06% | 0.04% | 0.00% | 0.00% |
| succinic acid | 87.87% | 90.72% | 85.51% | 88.63% | 88.80% | 91.52% |
| terephthalic acid | 0.00% | 0.00% | 0.00% | 0.00% | 0.00% | 0.00% |
| THF | 1.58% | 0.99% | 1.36% | 0.86% | 1.46% | 0.92% |

| | Rutile 1, 1/16" Time on Stream, hrs | | | | | |
|---|---|---|---|---|---|---|
| | 577 | | 723 | | 1009 | |
| | Mole % | Wt % | Mole % | Wt % | Mole % | Wt % |
| acetic acid | 0.13% | 0.07% | 0.46% | 0.24% | 0.14% | 0.08% |
| acrylic acid | 0.00% | 0.00% | 0.00% | 0.00% | 0.00% | 0.00% |
| 1,4-butanediol | 2.73% | 2.15% | 0.43% | 0.34% | 1.97% | 1.55% |
| 1-butanol | 0.00% | 0.00% | 0.00% | 0.00% | 0.00% | 0.00% |
| g-butyrolactone | 5.78% | 4.36% | 5.78% | 4.34% | 6.35% | 4.78% |
| fumaric acid | 0.01% | 0.01% | 0.00% | 0.00% | 0.00% | 0.00% |
| 4-hydroxybutyric acid | 2.38% | 2.17% | 2.39% | 2.16% | 1.36% | 1.24% |
| maleic acid | 0.00% | 0.00% | 0.00% | 0.00% | 0.00% | 0.00% |
| malic acid | 0.35% | 0.41% | 0.00% | 0.00% | 0.41% | 0.48% |
| methanol | 0.00% | 0.00% | 0.00% | 0.00% | 0.00% | 0.00% |
| 1,3-propanediol | 0.00% | 0.00% | 0.00% | 0.00% | 0.00% | 0.00% |
| propionic acid | 0.00% | 0.00% | 0.00% | 0.00% | 0.00% | 0.00% |
| succinic acid | 86.53% | 89.50% | 89.52% | 92.03% | 87.75% | 90.60% |
| terephthalic acid | 0.01% | 0.01% | 0.00% | 0.00% | 0.00% | 0.00% |
| THF | 2.09% | 1.32% | 1.42% | 0.89% | 2.02% | 1.27% |

TABLE 2b

Hydrogenation Results Using Rutile 1/8" Support and Pd Catalyst (Catalyst Example 2, 0.5% Pd on 1/8" Rutile Titanium Dioxide Support, 97% Rutile/3% Anatase) to convert Maleic Acid to Succinic Acid

| | Time on Stream, hrs | | | |
|---|---|---|---|---|
| | Rutile 2, 1/8" | | | |
| | 96 | | 238 | |
| | Mole % | Wt % | Mole % | Wt % |
| acetic acid | 0.23% | 0.12% | 0.24% | 0.12% |
| acrylic acid | 0.00% | 0.00% | 0.00% | 0.00% |
| 1,4-butanediol | 4.29% | 3.39% | 0.80% | 0.62% |
| 1-butanol | 2.91% | 1.90% | 0.17% | 0.11% |
| g-butyrolactone | 0.88% | 0.67% | 0.06% | 0.04% |
| fumaric acid | 0.00% | 0.00% | 0.00% | 0.00% |
| 4-hydroxybutyric acid | 0.00% | 0.00% | 0.00% | 0.00% |
| maleic acid | 0.00% | 0.00% | 0.00% | 0.00% |
| malic acid | 0.42% | 0.49% | 0.19% | 0.22% |
| methanol | 0.00% | 0.00% | 0.00% | 0.00% |
| 1,3-propanediol | 0.00% | 0.00% | 0.00% | 0.00% |
| propionic acid | 0.00% | 0.00% | 0.00% | 0.00% |
| succinic acid | 88.49% | 91.68% | 97.56% | 98.29% |
| terephthalic acid | 0.00% | 0.00% | 0.00% | 0.00% |
| THF | 2.77% | 1.76% | 0.98% | 0.60% |

Crush Strengths:

Crush strength is the most important indicator of the physical integrity and stability of the catalyst. Constant breaking of particles means problems with delta P, liquid flow, distribution problems, hot spots, etc. Measurements of single particle crush strength (SPCS) of some selected carbon extrudates and catalysts on carbon supports were made and compared with rutile TiO$_2$ extrudates and catalysts on the non-carbon rutile TiO$_2$ support using a Single Particle Crush Strength Test.

Single Particle Crush Strength Test

This test is applicable to carbon or other catalyst particles which are either extrudates or granules having a cylindrical geometry.

Apparatus—Sintech model 6 computer controlled mechanical testing unit and calipers.

Procedure—One-hundred particles of carbon are randomly selected by riffling a representative sample, which has been prepared following BDO-14 "Preparation of a Representative Sample for Analysis," and their lengths and widths measured in inches with calipers. The particles are stuck to an aluminum sheet and individually crushed in a Sintech 6 mechanical testing unit. A cross-head speed of 0.05 in/minute is used with a break sensitivity of 25%. In some cases premature cracking of the particle may occur before crushing and this load is recorded as the first visible peak on the load versus elongation curve. The single-particle crush strength data is analyzed as follows.

Load Per Unit Length—The failure stress is calculated by dividing the failure load of each particle (kg) by the length of the particle (mm). The percentage of particles failing at stresses <0.33 and <0.66 Kg/mm, and the mean failure stress, are calculated.

Results of crush strength tests are shown in Tables 3(a) and 3(b).

TABLE 3a

Crush Strength Comparisons

| Sample Tested | Average SPCS Kg/mm |
|---|---|
| 1.5 mm diameter Standard Carbon Extrudate, length > 3 mm | 1.26 |
| 1.5 mm diameter Standard Carbon Extrudate, length < 3 mm | 1.50 |
| 1.5 mm diameter BMC Standard Carbon Extrudate[1] | 1.51 |
| 1.8 mm diameter Carbon Extrudate | 1.7 |
| 1.5 mm diameter 98% Rutile/2% Anatase $TiO_2$ Extrudate | 7.71 |
| 3 mm diameter 97% Rutile/3% Anatase $TiO_2$ Extrudate | 12.92 |
| 3 mm diameter 83% Rutile/17% Anatase $TiO_2$ Extrudate | 1.72 |

[1]BMC (Broad Mill Cut) Carbon Extrudate is a cut taken from the middle range of lengths of the standard carbon extrudates.

The results in Table 3(a) show that the average crush strength of a 1.5 mm diameter titanium dioxide extrudate containing 98% rutile crystalline phase $TiO_2$ is about 5 times higher than the 1.5 mm diameter BMC standard carbon extrudate. The greater crush strength of the rutile $TiO_2$ catalyst support makes it more able to withstand the hot acid and high pressure conditions of the process of the invention without breaking or flaking than a similar carbon support or a support made of $TiO_2$ in the anatase crystalline phase, which is significantly less hard than the rutile crystalline phase $TiO_2$ and, therefore, more susceptible to flaking and breaking which increased delta P and reduces throughput in the reaction process.

TABLE 3b

Crush Strength Comparisons

| Support | SPCS Softest 1% Kg/mm | SPCS Softest 20% Kg/mm | SPCS Hardest 1% Kg/mm | Average SPCS Kg/mm |
|---|---|---|---|---|
| Standard Carbon, 15% of softest and hardest taken out, 1.5 mm diameter | 0.48 | <1.12 | 2.71 | 1.51 |
| Standard Carbon Catalyst, 0.4% Fe, 1.9% Na, 2.7% Pd, 10.0% Re, 2.7% Ag, 1.5 mm diameter | 0.43 | <0.60 | 1.37 | 0.76 |
| 94.5% Rutile $TiO_2$, 1.5 mm diameter | 1.87 | <3.31 | 6.52 | 4.06 |
| 77% Rutile $TiO_2$, 1.5 mm diameter | 0.63 | <2.27 | 6.87 | 3.15 |

The results in Table 3(b) show that the average crush strength of titanium dioxide extrudates containing 77% rutile crystalline phase is 2.09 times greater than a standard carbon extrudate and 4.14 times greater than standard carbon with catalyst metals on it. The average crush strength of the 94.5% rutile crystalline phase $TiO_2$ extrudate is 2.69 times greater than the standard carbon extrudate and 5.34 times greater than standard carbon with catalyst metals on it.

The carbon-based catalyst manufacturing procedure, which requires more than one step, further hurts the SPCS as can be seen from the reduced crush strength of the carbon extrudate having the catalyst metals on it. In the case of the rutile $TiO_2$ catalyst support, the simple one-step preparation will help preserve the hardness. This increased physical integrity and stability may further improve catalyst life and the delta P.

Example 4

2.0% Pd/5.0% Re on 1/16" Rutile Titanium Dioxide Support (94% Rutile/6% Anatase Crystalline Phase)

The catalyst of Example 4 is made by the same procedure as the catalyst of Example 1(a) except that the amounts of palladium and rhenium are adjusted to give a catalyst containing 2.0 wt % palladium and 5.0 wt % rhenium.

Table 4 shows the results of the second stage hydrogenation of succinic acid to 1,4-Butanediol (BDO). The first stage reaction (not shown) wherein maleic acid was converted to succinic acid was conducted using a catalyst comprising 0.5% palladium on a 1/8" rutile $TiO_2$ support, such as the catalyst of Example 2, and the second stage reaction was conducted using a catalyst made by the process of Example 4, comprising 2.0% Pd and 5% Re on a 1/16" rutile titanium dioxide support.

TABLE 4

| Run Description | TOS, hr | Liq. Rate, cc/hr | 2nd Stage Rxr Activity, in °C. | Selectivity, wt % | | | | |
|---|---|---|---|---|---|---|---|---|
| | | | | BDO | GBL | SAC | THF | BuOH |
| 2nd stage: | 90 | 16 | 188° C. | 14.44 | 0.00 | 0.14 | 39.38 | 40.85 |
| Catalyst Example 4; | 105 | 16 | 187° C. | 19.95 | 0.00 | 0.04 | 36.37 | 40.04 |
| 2.0% Pd/5% Re on | 129 | 16 | 184° C. | 36.8 | 0.00 | 0.04 | 29.10 | 30.32 |
| 1/16" rutile $TiO_2$ | 249 | 16 | 180° C. | 61.37 | 0.00 | 0.07 | 18.55 | 17.73 |
| (94% rutile) | 273 | 16 | 180° C. | 50.64 | 0.00 | 0.04 | 22.76 | 23.80 |
| | 297 | 16 | 175° C. | 58.25 | 0.00 | 0.04 | 13.28 | 11.77 |
| | 417 | 16 | 170° C. | 74.71 | 0.00 | 0.03 | 16.26 | 8.23 |
| | 441 | 16 | 170° C. | 75.84 | 0.00 | 0.03 | 15.76 | 7.29 |
| | 465 | 16 | 165° C. | 77.13 | 0.12 | 0.06 | 15.24 | 6.64 |
| | 513 | 20 | 165° C. | 75.63 | 1.16 | 0.15 | 16.24 | 5.73 |
| | 585 | 20 | 165° C. | 66.23 | 10.64 | 0.51 | 17.46 | 4.50 |
| | 609 | 20 | 165° C. | 65.57 | 12.18 | 0.59 | 16.87 | 4.21 |
| | 633 | 20 | 165° C. | 62.57 | 13.72 | 0.66 | 18.02 | 4.61 |
| | 801 | 16 | 165° C. | 74.36 | 0.00 | 0.05 | 16.18 | 8.48 |
| | 825 | 16 | 165° C. | 72.44 | 0.00 | 0.03 | 17.81 | 8.80 |
| | 849 | 16 | 165° C. | 77.70 | 0.00 | 0.03 | 14.44 | 6.94 |
| | 921 | 18 | 165° C. | 74.70 | 2.94 | 0.16 | 15.96 | 5.52 |
| END OF RUN | 945 | 18 | 165° C. | 76.75 | 4.47 | 0.18 | 12.98 | 5.03 |

Example 5

0.5% Pd/5.0% Re on 1/16" Rutile Titanium Dioxide Support (94% Rutile/6% Anatase Crystalline Phase)

The Example 5(a) is made by the same procedure as the catalyst of Example 1(a) except that the amounts of palladium and rhenium are adjusted to give a catalyst containing 0.5 wt % palladium and 5.0 wt % rhenium.

Example 5(b)

0.5% Pd/5.0% Re on 1/16" Rutile Titanium Dioxide Support (98% Rutile/2% Anatase Crystalline Phase)

The catalyst of Example 5(b) is made by the procedure of Example 5(a) except that a 1/16" diameter rutile TiO$_2$ support (98% Rutile/2% Anatase Crystalline Phase) is used.

TABLE 5

Activity and Selectivity for 2$^{nd}$-stage, rutile-supported catalyst formulations

| Run Description | TOS, hr | Liq. Rate, cc/hr | 2nd Stage Rxr Activity, in ° C. | Selectivity, wt % | | | | |
|---|---|---|---|---|---|---|---|---|
| | | | | BDO | GBL | SAC | THF | BuOH |
| 2nd stage: Catalyst Example 5; 0.5% Pd/5% Re on 1/16" rutile TiO$_2$ (94% rutile) | 112 | 32 | 165° C. | 18.8 | 66.42 | 11.89 | 1.84 | 0.89 |
| | 135 | 32 | 175° C. | 37.81 | 52.55 | 4.84 | 2.46 | 2.02 |
| | 159 | 32 | 180° C. | 50.01 | 38.12 | 2.94 | 5.31 | 3.10 |
| | 183 | 32 | 185° C. | 58.61 | 27.86 | 1.75 | 7.11 | 4.18 |
| | 208 | 32 | 185° C. | 56.03 | 30.02 | 1.97 | 7.31 | 3.88 |
| | 281 | 24 | 185° C. | 72.85 | 11.17 | 0.53 | 7.85 | 6.30 |
| | 303 | 24 | 185° C. | 70.80 | 8.46 | 0.39 | 10.84 | 8.21 |
| | 327 | 24 | 185° C. | 72.90 | 8.86 | 0.44 | 10.33 | 6.32 |
| | 447 | 16 | 185° C. | 66.38 | 0.12 | 0.06 | 14.75 | 16.09 |
| | 471 | 16 | 175° C. | 76.13 | 8.49 | 0.36 | 7.51 | 5.98 |
| END OF RUN | 495 | 16 | 177° C. | 78.24 | 5.19 | 0.21 | 8.73 | 6.26 |

Table 5 shows the results of the second stage hydrogenation of succinic acid to 1,4-Butanediol (BDO). The first stage reaction (not shown) wherein maleic acid was converted to succinic acid was conducted using a catalyst comprising 0.5% palladium on a 1/8" rutile TiO$_2$ support, such as the catalyst of Example 2, and the second stage reaction was conducted using a catalyst made by the process of Example 5 comprising 0.5% Pd and 5% Re on a 1/16" rutile titanium dioxide support.

Example 6

0% Pd/5.0% Re on 1/16" Rutile Titanium Dioxide Support (94% Rutile/6% Anatase Crystalline Phase)

The catalyst of Example 6 is made by the same procedure as the catalyst of Example 1(a) except that palladium is not used and the amount of rhenium is adjusted to give a catalyst containing and 5.0 wt % rhenium.

TABLE 6

Activity and Selectivity for 2$^{nd}$-stage, rutile-supported catalyst formulations

| Run Description | TOS, hr | Liq. Rate, cc/hr | 2nd Stage Rxr Activity, in ° C. | Selectivity, wt % | | | | |
|---|---|---|---|---|---|---|---|---|
| | | | | BDO | GBL | SAC | THF | BuOH |
| 2nd stage: Catalyst Example 6; 0.0% Pd/5% Re on 1/16" rutile TiO$_2$ (94% rutile) | 90 | 16 | 185° C. | 87.56 | 1.36 | 0.06 | 4.64 | 5.44 |
| | 113 | 16 | 170° C. | 71.82 | 19.50 | 0.70 | 4.19 | 3.01 |
| | 137 | 16 | 175° C. | 79.95 | 10.38 | 0.35 | 5.17 | 3.49 |
| | 161 | 16 | 176° C. | 79.62 | 10.42 | 0.37 | 5.16 | 3.68 |
| | 186 | 16 | 177° C. | 78.33 | 9.64 | 0.37 | 6.61 | 4.19 |
| | 249 | 16 | 178° C. | 87.29 | 0.00 | 0.09 | 5.52 | 5.21 |
| | 273 | 16 | 180° C. | 88.34 | 0.00 | 2.38 | 3.90 | 4.42 |
| | 297 | 16 | 179° C. | 88.18 | 0.00 | 0.13 | 5.83 | 4.57 |

TABLE 6-continued

Activity and Selectivity for 2nd-stage, rutile-supported catalyst formulations

| Run Description | TOS, hr | Liq. Rate, cc/hr | 2nd Stage Rxr Activity, in ° C. | Selectivity, wt % | | | | |
|---|---|---|---|---|---|---|---|---|
| | | | | BDO | GBL | SAC | THF | BuOH |
| | 321 | 16 | 177° C. | 81.65 | 6.88 | 1.18 | 5.24 | 3.89 |
| | 441 | 16 | 177° C. | 89.15 | 1.82 | 0.07 | 3.38 | 4.71 |
| | 465 | 16 | 172° C. | 81.91 | 10.14 | 0.32 | 4.04 | 2.86 |
| | 609 | 16 | 173° C. | 75.16 | 17.48 | 0.61 | 3.24 | 2.90 |
| | 633 | 16 | 173° C. | 80.14 | 11.07 | 0.30 | 4.98 | 3.01 |
| | 657 | 16 | 173° C. | 73.60 | 17.67 | 0.39 | 4.88 | 2.88 |
| | 681 | 16 | 173° C. | 78.61 | 4.95 | 0.21 | 8.83 | 6.28 |
| END OF RUN >>>> | 825 | 16 | 173° C. | 64.14 | 25.74 | 1.05 | 5.66 | 2.89 |

Table 6 shows the results of the second stage hydrogenation of succinic acid to 1,4-Butanediol (BDO). In this reaction the first stage reaction wherein maleic acid was converted to succinic acid was conducted using a standard carbon catalyst, such as Carbon Catalyst B, and the second stage reaction was conducted using a catalyst comprising 0% Pd and 5% Re on a 1/16" rutile titanium dioxide support.

Example 7

1.0% Pd/3% Re on 1/16" Rutile Titanium Dioxide Support (94% Rutile/6% Anatase Crystalline Phase)

The catalyst of Example 7 is made by the same procedure as the catalyst of Example 1(a) except that the amounts of palladium and rhenium are adjusted to give a catalyst containing 1.0 wt % palladium and 3.0 wt % rhenium.

TABLE 7

Activity and Selectivity for 2nd-stage, rutile-supported catalyst formulations

| Run Description | TOS, hr | Liq. Rate, cc/hr | 2nd Stage Rxr Activity, in ° C. | Selectivity, wt % | | | | |
|---|---|---|---|---|---|---|---|---|
| | | | | BDO | GBL | SAC | THF | BuOH |
| 2nd stage: Catalyst | 21 | 16 | 185° C. | 81.5 | 0.00 | 0.04 | 2.95 | 14.1 |
| Example 7; 1.0% Pd/ | 45 | 16 | 175° C. | 88.7 | 1.59 | 0.09 | 3.05 | 5.73 |
| 3% Re on 1/16" rutile | 141 | 16 | 170° C. | 86.9 | 4.65 | 0.17 | 4.16 | 3.61 |
| TiO$_2$ (94% rutile) | 165 | 16 | 168° C. | 84.6 | 6.79 | 0.25 | 4.45 | 3.35 |
| | 195 | 16 | 168° C. | 87.4 | 0.53 | 0.11 | 5.79 | 5.63 |
| | 213 | 16 | 166° C. | 87.4 | 2.48 | 0.11 | 5.41 | 4.10 |
| END OF RUN> | 237 | 16 | 164° C. | 84.7 | 5.04 | 0.20 | 5.71 | 3.74 |

Table 7 shows the results of the second stage hydrogenation of succinic acid to 1,4-Butanediol (BDO). In this reaction the first stage reaction wherein maleic acid was converted to succinic acid was conducted using a standard carbon catalyst, such as Carbon Catalyst B, and the second stage reaction was conducted using a catalyst comprising 1.0% Pd and 3% Re on a 1/16" rutile titanium dioxide support.

Tables 4, 5, 6, and 7 show the results of testing catalysts of the invention in the second stage reaction wherein succinic acid is hydrogenated to produce 1,4-butanediol, gamma-butyrolactone, and/or tetrahydrofuran using a catalyst comprising at least one hydrogenation catalyst component on a rutile titanium dioxide support. It can be seen from the results in Tables 4, 5, 6, and 7 that the catalyst of the present invention shows good selectivity for 1,4-butanediol.

Example 8

Two-step 2.0% Pd/5.0% Re on Rutile Catalyst Preparation (A) Rutile TiO$_2$ Support (94% Rutile, 6% Anatase, 1/16") rutile titanium dioxide 93.0 g (dry)
(B) Pd/HNO$_3$ Impregnation Solution
    9.48 g of Pd (NO$_3$)$_2$ Solution (21.1% Pd)
    10.07 g of concentrated nitric acid (70 wt %)
(C) Re/HNO$_3$ Impregnation Solution
    9.09 g HReO$_4$ Solution (54.98% Re)
    10.46 g of concentrated nitric acid (70 wt %)

Preparation Procedure:
Step 1: The rutile TiO$_2$ support (A) is gradually impregnated with solution (B) and allowed to stand for 1 hour. The material is then dried in an oven at 130° C. for 2 hours.
Step 2: The palladium-impregnated TiO$_2$ rutile support (A) from Step 1 is gradually impregnated with solution (C) and allowed to stand for 1 hour. The material is then dried in an oven at 130° C. for 2 hours.
The results for the stage 1 reaction converting maleic acid to succinic acid are shown in Table 8(a), in which a sample was taken at 139 hours. The results for the second stage reaction converting succinic acid to BDO, THF, and GBL or mixtures thereof over several hours is shown in Table 8(b).

TABLE 8(a)

Activity and Selectivity for 1st-stage, rutile-supported catalyst formulations

| Run Description | TOS, hr | Liq. Rate, cc/hr | 1st Stage Rxr Activity, in °C. | BDO | GBL | SAC | THF | BuOH |
|---|---|---|---|---|---|---|---|---|
| | | | | | Selectivity, wt % | | | |
| 1st stage: Catalyst Example 8 - 2.0% Pd/5.0% Re on 1/16" rutile TiO$_2$ (94% rutile) | 138 | 24 | 110° C. | 0.0 | 21.55 | 72.89 | 4.07 | 0.00 |

Table 8a shows the results of the first stage hydrogenation of maleic acid to succinic acid (SAC) using a catalyst comprising 2.0% Pd and 5.0% Re on a 1/16" rutile titanium dioxide support.

TABLE 8(b)

Activity and Selectivity for 2$^{nd}$-stage, rutile-supported catalyst formulations

| Run Description | TOS, hr | Liq. Rate, cc/hr | 2nd Stage Rxr Activity, in °C. | BDO | GBL | SAC | THF | BuOH |
|---|---|---|---|---|---|---|---|---|
| | | | | | Selectivity, wt % | | | |
| 2nd stage: Catalyst Example 8 - 2.0% Pd/5.0% Re on 1/16" rutile TiO$_2$ (94% rutile) | 68 | 24 | 165° C. | 71.99 | 10.05 | 0.30 | 12.52 | 4.44 |
| | 89 | 24 | 165° C. | 71.14 | 9.73 | 0.29 | 14.02 | 4.30 |
| | 114 | 24 | 165° C. | 69.90 | 10.33 | 0.33 | 14.76 | 4.14 |
| | 235 | 24 | 165° C. | 62.45 | 13.82 | 0.61 | 19.39 | 4.30 |
| | 257 | 22 | 165° C. | 68.33 | 9.24 | 0.36 | 17.41 | 4.15 |
| END OF RUN | 281 | 20 | 165° C. | 71.14 | 4.72 | 0.17 | 18.65 | 4.66 |

Table 8b shows the results of the second stage hydrogenation of succinic acid to 1,4-Butanediol (BDO) using a catalyst comprising 2.0% Pd and 5.0% Re on a 1/16" rutile titanium dioxide support.

Example 9

Example 9 - 1$^{st}$-Stage Material 10 0.5% Pd on 1/16" Rutile Catalyst Preparation Materials:
Rutile TiO$_2$ Support (94% Rutile, 6% Anatase 1/16 inch (1.5 mm) diameter)

Titanium dioxide containing 96 wt % of the rutile crystalline phase of titanium dioxide and 6 wt % of the anatase crystalline phase of titanium dioxide, 49.5 g (dry).

Pd Impregnation Solution 1.31 g of Pd (NO$_3$)$_2$ Solution (19.02 wt % Pd) is mixed with 6.12 g concentrated nitric acid (70% nitric acid). This solution is used to impregnate the 96% rutile titanium dioxide support.

Preparation Procedure:

Step 1

The 96% rutile titanium dioxide support is gradually impregnated with the Pd impregnation solution, and allowed to stand for 1 hr. The material is then dried in an oven at 130° C. for 3.5 hr.

Example 9 - 2nd-Stage Material

Carbon Catalyst—Aqueous Two-step Preparation of BDO Catalyst with 1.5 mm Carbon Support This procedure describes an aqueous two-step BDO catalyst preparation using Norit 1.5 mm carbon. Nominal Composition: 0.4% Fe, 1.9% Na, 2.66% Ag, 2.66% Pd, 10.0% Re on 1.5 mm diameter carbon.

Materials:
(A) Carbon Support:

58.4 g of Norit 1.5 mm diameter Active Carbon extrudate (referred to herein as Standard C or standard carbon) (acquired from Norit Americas Inc. located in Atlanta, Ga.)

(B) Ag/Fe/Na Impregnation Solution:

2.9 g of silver nitrate, 5.1 g of sodium nitrate and 2 g of [Fe(NO$_3$)$_3$.9H$_2$O] are dissolved in 20 g of de-ionized water and then gradually mixed with 68.3 g of concentrated nitric acid (70 wt % nitric acid).

(C) Pd/Re Impregnation Solution 1:

9.1 g of Pd (NO$_3$)$_2$ solution (20.38% Pd), 12.22 g of HReO$_4$ solution (56.36 wt % Re), 23.3 g of concentrated nitric acid (70 wt % nitric acid), and 24 g of de-ionized water are mixed together.

Preparation Procedure:

Step 1

The carbon support (A) is gradually impregnated with the Ag/Fe/Na impregnation solution (B), and allowed to stand for 1 hr. The material is then dried in an oven at 130° C. for 4.5 hr.

Step 2

The carbon support (A) which has been impregnated with Ag/Fe/Na is next gradually impregnated with the Pd/Re solution (C) and the mixture is allowed to stand for 3 hr. The catalyst is then dried for 5 hr at 130° C.

The rutile titanium dioxide support is gradually impregnated with the Pd/Re impregnation solution, and allowed to stand for 1 hr. The material is then dried in an oven at 130° C. for 3.5 hr.

TABLE 9

Conversion of Maleic Acid (MAC) to Succinic Acid (SAC) with Catalyst Example 9 (0.5% Pd, edge-coated on 1/16" Rutile) and Conversion of SAC from the 1$^{st}$ stage reaction to BDO, GBL, and THF with a Standard Carbon Catalyst B - (0.4% Fe, 1.9% Na, 2.66% Ag, 2.66% Pd, 10.0% Re on 1.5 mm carbon support).

| Results | 1$^{st}$ Stage Reaction Composition | | 2$^{nd}$ Stage Reaction |
|---|---|---|---|
| | Catalyst Example 9 - 0.5% Pd edge-coated on (98% Rutile, 2% Anatase, 1/16 inch diameter) support | | Standard Carbon Catalyst B - 0.4% Fe, 1.9% Na, 2.66% Ag, 2.66% Pd, 10.0% Re on 1.5 mm carbon support |
| | Mole % | Wt % | |
| acetic acid | 0.04% | 0.02% | |
| acrylic acid | 0.00% | 0.00% | |
| 1,4-butanediol | 0.31% | 0.24% | 90.71 wt % |
| 1-butanol | 0.41% | 0.26% | |
| g-butyrolactone | 0.52% | 0.38% | 0 |
| fumaric acid | 0.00% | 0.00% | |
| 4-hydroxybutyric acid | 0.06% | 0.05% | |
| maleic acid | 0.00% | 0.00% | |
| malic acid | 0.00% | 0.00% | |
| methanol | 0.00% | 0.00% | |
| 1,3-propanediol | 0.00% | 0.00% | |
| propionic acid | 0.00% | 0.00% | |
| succinic acid | 97.41% | 98.28% | 0.26 wt % |
| B-s ester and S-HBA ester | 0.00% | 0.00% | |
| THF | 1.25% | 0.77% | 4.98 wt % |
| BDO + GBL + THF | | | 95.9 wt % |
| Time on Stream | hrs. | | 1009 hrs. |
| Liquid Hourly Space Velocity | 1.6 | | 0.8 |
| MAC Conversion, % | 100 | | n.a. |
| SAC selectivity | | 98.28% | 0.26 |

That which is claimed is:

1. A process for the production of at least one of 1,4-butanediol, gamma-butyrolactone, and tetrahydrofuran comprising catalytically hydrogenating a hydrogenatable precursor in contact with a hydrogen-containing gas and a hydrogenation catalyst comprising palladium on a catalyst support comprising titanium dioxide, wherein the titanium dioxide is formed by calcination of titanium dioxide at a temperature of from about 600°C. to about 1200°C. such that at least about 70 weight percent of said titanium dioxide is in the rutile crystalline phase.

2. The process of claim 1 wherein the hydrogenation catalyst further comprises at least one of platinum, rhodium and ruthenium.

3. The process of claim 1, wherein the hydrogenation catalyst comprises palladium and rhenium.

4. The process of claim 1, wherein the hydrogenation catalyst comprises palladium and rhenium on a catalyst support comprising titanium dioxide, wherein at least about 85 weight percent of said titanium dioxide is in the rutile crystalline phase.

5. The process of claim 1 wherein the hydrogenatable precursor is selected from the group consisting of maleic acid, maleic anhydride, fumaric acid, succinic anhydride, succinic acid, dimethyl succinate, gamma-butyrolactone and mixtures thereof.

6. The process of claim 1 wherein the hydrogenatable precursor is selected from the group consisting of maleic acid, maleic anhydride, succinic acid, succinic anhydride and mixtures thereof.

7. The process of claim 1 wherein at least 90 weight percent of the titanium dioxide is in the rutile crystalline phase.

8. The process of claim 1 wherein at least 95 weight percent of the titanium dioxide is in the rutile crystalline phase.

9. The process of claim 4 wherein at least 90 weight percent of the titanium dioxide is in the rutile crystalline phase.

10. The process of claim 4 wherein at least 95 weight percent of the titanium dioxide is in the rutile crystalline phase.

11. The process of claim 1, wherein the ratio of hydrogen to hydrogenatable precursor is between about 5 to 1 and about 1000 to 1.

12. The process of claim 1, wherein the hydrogen-containing gas pressure is between about 20 and 400 atmospheres.

13. The process of claim 1, wherein the process is conducted at a temperature of from about 500° C. to about 350° C.

14. The process of claim 1, wherein the process is conducted at a temperature of from about 50° C. to about 250° C.

15. The process of claim 1, wherein the contact time is between about 0.1 minute and 20 hours.

16. The process of claim 1, wherein the catalyst comprises from about 0.01 to about 20 weight percent palladium.

17. The process of claim 1, wherein the catalyst comprises from about 0.05 to about 8 weight percent palladium.

18. The process of claim 4, wherein the catalyst comprises from about 0.01 to about 20 weight percent palladium and from about 0.1 to about 20 weight percent rhenium.

19. The process of claim 4, wherein the catalyst comprises from about 0.2 to about 5 weight percent palladium and from about 0.5 to about 10 weight percent rhenium.

20. A process for the production of at least one of 1,4-butanediol, gamma-butyrolactone, and tetrahydrofuran comprising catalytically hydrogenating a hydrogenatable precursor selected from the group consisting of maleic acid, maleic anhydride, succinic acid, succinic anhydride and mixtures thereof in contact with a hydrogen-containing gas and a hydrogenation catalyst comprising palladium and rhenium on a catalyst support comprising titanium dioxide, wherein the titanium dioxide is formed by calcination of titanium dioxide at a temperature of from about 600°C. to about 1200°C. such that at least about 90 weight percent of said titanium dioxide is in the rutile crystalline phase.

21. The process of claim 20 wherein the process is conducted at a temperature of from about 50° C. to about 350° C., wherein the hydrogen-containing gas pressure is between about 20 and 400 atmospheres, and wherein the contact time is between about 0.1 minute and 20 hours.

22. The process of claim 21, wherein the catalyst comprises from about 0.01 to about 20 weight percent palladium and from about 0.1 to about 20 weight percent rhenium.

23. The process of claim 21, wherein the catalyst comprises from about 0.05 to about 8 weight percent palladium and from about 0.5 to about 10 weight percent rhenium.

24. The process of claim 21, wherein the catalyst comprises from about 0.1 to about 5 weight percent palladium and from about 0.5 to about 7 weight percent rhenium.

25. The process of claim 1 further comprising:
(A) a first hydrogenation zone and a second hydrogenation zone connected in series,
(B) supplying to the first hydrogenation zone a feedstream comprising a hydrogenatable precursor selected from the group consisting of maleic acid, maleic anhydride, fumaric acid, and mixtures thereof,
(C) reacting in the first hydrogenation zone, the hydrogenatable precursor feedstock and hydrogen in contact with a catalyst comprising palladium on a catalyst support comprising titanium dioxide, wherein at least about 70 weight percent of said titanium dioxide is in the rutile crystalline phase, to produce a reaction product comprising succinic acid,
(D) supplying to the second hydrogenation zone, the reaction product of the first hydrogenation zone,
(E) reacting in the second hydrogenation zone, the reaction product from the first hydrogenation zone and hydrogen in contact with a catalyst comprising palladium and rhenium on a catalyst support comprising titanium dioxide, wherein at least about 70 weight percent of said titanium dioxide is in the rutile crystalline phase to produce a product stream comprising at least one of 1,4-butanediol, gamma-butyrolactone, and tetrahydrofuran,
wherein the temperature of the feedstream comprising maleic acid and the temperature of the first hydrogenation zone are controlled such that the temperature of maleic acid in the feedstream and the first hydrogenation zone does not exceed about 130° C.

26. The process of claim 25 wherein the catalyst of step (C) comprises palladium and rhenium on a catalyst support comprising titanium dioxide, wherein at least about 90 weight percent of said titanium dioxide is in the rutile crystalline phase, and the catalyst of step (E) comprises palladium and rhenium on a catalyst support comprising titanium dioxide, wherein at least about 90 weight percent of said titanium dioxide is in the rutile crystalline phase.

27. The process of claim 25 wherein the temperature in the first reaction zone is from about 50° C. to about 130° C. and the temperature in the second reaction zone is from about 100° C. to about 300° C.

28. The process of claim 1 further comprising:
(A) a first hydrogenation zone and a second hydrogenation zone connected in series,
(B) supplying to the first hydrogenation zone a feedstream comprising maleic acid,
(C) reacting in the first hydrogenation zone, the maleic acid feedstock and hydrogen in contact with a catalyst comprising palladium on a catalyst support comprising titanium dioxide, wherein at least about 70 weight percent of said titanium dioxide is in the rutile crystalline phase, to produce a reaction product comprising succinic acid,
(D) supplying to the second hydrogenation zone, the reaction product of the first hydrogenation zone,
(E) reacting in the second hydrogenation zone, the reaction product from the first hydrogenation zone and hydrogen in contact with either:
(a) a catalyst comprising palladium and rhenium on a catalyst support comprising titanium dioxide, wherein at least about 70 weight percent of said titanium dioxide is in the rutile crystalline phase,
(b) a catalyst comprising palladium and rhenium on a carbon support to produce a product stream comprising at least one of 1,4-butanediol, gamma-butyrolactone, and tetrahydrofuran, or
(c) mixtures of the catalysts of (a) and (b);
wherein the temperature of the feedstream comprising maleic acid and the temperature of the first hydrogenation zone are controlled such that the temperature of maleic acid in the feedstream and the first hydrogenation zone does not exceed about 130° C.

29. The process of claim 28 wherein the catalyst of step (C) comprises palladium and rhenium on a catalyst support comprising titanium dioxide, wherein at least about 90 weight percent of said titanium dioxide is in the rutile crystalline phase, and the catalyst of step (E) is either:
(a) a catalyst comprising palladium and rhenium on a catalyst support comprising titanium dioxide, wherein at least about 90 weight percent of said titanium dioxide is in the rutile crystalline phase,
(b) a catalyst comprising palladium and rhenium on a carbon support, or
(c) mixtures of the catalysts of (a) and (b).

30. The process of claim 28 wherein the temperature in the first reaction zone is from about 50° C. to about 130° C. and the temperature in the second reaction zone is from about 100° C. to about 300° C.

31. The process of claim 1 wherein the catalyst support comprising titanium dioxide has a total specific surface area of less than about 40 square meters per gram.

* * * * *